United States Patent [19]

Carlson

[11] Patent Number: 4,936,904
[45] Date of Patent: Jun. 26, 1990

[54] ARYL-4-OXONICOTINATES USEFUL FOR INDUCING MALE STERILITY IN CEREAL GRAIN PLANTS

[76] Inventor: Glenn R. Carlson, 305 Britt Rd., North Wales, Pa. 19454

[21] Appl. No.: 128,010

[22] Filed: Dec. 2, 1987

Related U.S. Application Data

[63] Continuation of Ser. No. 509,981, Jul. 1, 1983, Pat. No. 4,714,492, which is a continuation of Ser. No. 260,577, May 5, 1981, abandoned, which is a continuation-in-part of Ser. No. 148,079, May 12, 1980, abandoned.

[51] Int. Cl.$^5$ .................... C07D 211/84; A01N 43/40
[52] U.S. Cl. ........................................ 71/94; 546/298; 546/316
[58] Field of Search ............................ 546/298; 71/94

[56] References Cited

U.S. PATENT DOCUMENTS

| | | | |
|---|---|---|---|
| 3,576,814 | 4/1971 | Seidel | 546/298 |
| 3,761,240 | 9/1973 | Seidel | 71/76 |
| 3,831,815 | 9/1974 | Seidel | 546/298 |
| 4,028,084 | 3/1977 | McNulty | 71/94 |
| 4,051,142 | 4/1977 | Carlson | 546/298 |
| 4,115,101 | 9/1978 | Carlson | 71/94 |
| 4,152,136 | 5/1979 | Taylor | 71/90 |
| 4,714,492 | 12/1987 | Carlson | 71/94 |

FOREIGN PATENT DOCUMENTS

| | | | |
|---|---|---|---|
| 1A003144 | 1/1979 | European Pat. Off. | 546/298 |
| 2830700 | 2/1979 | Fed. Rep. of Germany | 546/298 |
| 2395996 | 1/1979 | France | 71/94 |
| 12029403 | 3/1980 | United Kingdom | 546/298 |
| 2013190 | 7/1982 | United Kingdom | 546/288 |

OTHER PUBLICATIONS

Taylor, Chem. Abstracts, vol. 91 (21), Abst. No. 175,206c, Nov. 19, 1979.
Wick, Chem. Abstracts, vol. 91 (25), Abst. No. 211,273h, Dec. 17, 1979.
Chem. Abs., 93:199231z (1980).
Chem. Abs., 89:129415f (1978).
Chem. Abs., 89:129420d (1978).
Chem. Abs., 91:211273h (1979).
Selva et al., *Org. Mass Spectrometry*, 11(2), 117 (1976); *Chem. Abs.*, 85:76951m (1976).
Caramella et al., *Chim. Ind. Milan*, 53, 556 (1971).
Caramella et al., *Tetrahedron*, 27, 379 (1971).
R. Johnstone et al., *Aust. J. Chem.*, 11, 562 (1958); *Chem. Abs.*, 53:5310d (1968).
I. Adachi, *Chem. Parm. Bull.*, 17, 2209 (1969).
T. Kametani et al., *J. Het. Chem.*, 14, 477 (1977).
R. P. Abdulla, *Synthetic Communications* 7, 313 (1977).
Caramella et al., *Synthesis*, 46–47 (1972) *Chem. Abs.*, 76:113,032Z (1972).
Balogh et al., *J. Het. Chem.*, 17, 359 (1980).
Riaz et al., Chem. Abstracts 87:184,333m (1977).
Gennaro et al., Chem Abstracts 85:76951 (1976).
Chem. Abstracts 91:175,206 (1979) (Taylor).
Chem Abstracts 91:211,273b (1979) (Wick).

*Primary Examiner*—Alan L. Rotman
*Attorney, Agent, or Firm*—Robert B. Martin

[57] ABSTRACT

The present invention relates to N-alkyl-2-aryl-4-oxonicotinates, N-alkyl-5-aryl-4-oxonicotinates, N-alkyl-6-aryl-4-oxonicotinates and N-alkyl-2,6-diaryl-4-oxonicotinates and their use as plant hybridization agents especially useful in wheat, barley and corn. These compounds are particularly active as chemical gametocides and possess a high degree of male/female selectivity. Moreover, these compounds are relatively noninjurious to both corn and wheat crops. The fact that these chemicals possess a high degree of male sterility without affecting female fertility makes them very useful as chemical gametocides.

2 Claims, No Drawings

ARYL-4-OXONICOTINATES USEFUL FOR INDUCING MALE STERILITY IN CEREAL GRAIN PLANTS

This is a continuation of application Ser. No. 509,981, filed July 1, 1983, now U.S. Pat. No. 4,714,492, which is a continuation of application Ser. No. 260,577, filed May 5, 1981, now abandoned, which is a continuation-in-part of application Ser. No. 148,079, filed May 12, 1980, now abandoned.

BACKGROUND OF THE INVENTION

The use of chemical gametocides for the production of new cereal grains is a rapidly expanding technology. Cereal grain such as corn, wheat, rice, rye, barley, millet, sorghum, triticale and various forage crops are the main areas where research has been undertaken to improve both the productivity and the food value of these crops. The utilization of chemical hybridization agents in this research has made possible the hybridization of cereal grain crops on economical scale. Patents which pertain to this technology include the Michael C. Seidel U.S. Pat. Nos. 3,761,240; 3,838,155; and 3,576,814, which disclose N-aryl-2-oxonicotinates as male sterilants and plant growth regulators; the Glenn R. Carlson U.S. Pat. Nos. 4,115,101; 4,051,142; and German Offen. 2,830,700, which disclose the use of N-aryl-4-oxonicotinate and N-aryl-6-oxonicotinates as male sterilants; and the Taylor U.S. Pat. No. 4,152,136, which discloses the use of 3-aryl-4-pyridones as herbicides. A. Selva and A. Gennaro describe in *Organic Mass Spectrometry*, Vol. 11, pp 117–120 (1976) the mass spectrometry data for the compound 2-phenyl-6-methyl-3-carbethoxy-4-pyridone. No activity is disclosed for this compound.

Balogh et al. *J. Het. Chem.*, 17, 359 (1980), disclose the synthesis of various 5-substituted (5-aryl)-1-alkyl-4-oxo-1,4-dihydro-3-pyridine carboxylic acid derivatives for antimicrobial studies.

R. Johnstone et al., *Aust. J. Chem.*, 11, 562 (1968) (*Chem. Abs.*, 53, 5310d (1968)) disclose 1-methyl-6-phenyl-4-pyridone-3-carboxylic acid as a decarboxylation product of a quinolone compound.

T. Kametani et al., *J. Het. Chem.*, 14, 477 (1977) disclose the synthesis of various 1,4-dihydro-4-oxonicotinic acid derivatives, some of which bear a 6-phenyl group, which compounds have antibacterial properties.

Wick et al., Ger. Offen. 2,901,868 (*Chem. Abs.*, 91, 211273h (1979)) disclose 4-pyridone-3-carboxylic acid derivatives, for example, the 6-phenyl derivative thereof, which possess bactericidal and central nervous system stimulant properties.

Adachi, *Chem - Pharm. Bull.*, 17 (11), 2209 (1969), discloses ring conversion reactions of isoxazolium salts, two of the products of which are ethyl 6-phenyl-1,2,5-trimethyl-4-pyridone-3-carboxylate and 6-phenyl-1,2,5-trimethyl-4-pyridone-3-carboxylic acid. No biological activity is disclosed.

Kigasawa et al., Japan Kokai 78 65,882 (*Chem. Abs.*, 89, 129415f (1978) disclose several 1,4-dihydro-4-oxonicotinic acids having antibacterial activity. Among the compounds disclosed are 6-phenyl-5-methyl-1-ethyl-1,4-dihydro-4-oxonicotinic acid, 6-methyl-5-phenyl-1-ethyl-1,4-dihydro-4-oxonicotinic acid, and 5,6-diphenyl-1-ethyl-1,4-dihydro-4-oxonicotinic acid.

SUMMARY OF THE INVENTION

This invention relates to compounds of the formula:

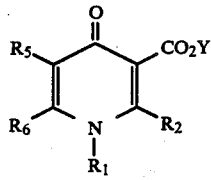

(I)

wherein $R_1$ is an optionally substituted ($C_1$–$C_6$) alkyl or ($C_2$–$C_6$) alkenyl group; at least one of $R_2$, $R_5$ and $R_6$ is

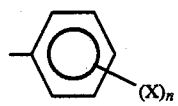

wherein
(1) when $R_2$ is

$R_5$ is a hydrogen atom, an alkyl group or a halogen atom and $R_6$ is a hydrogen atom or an alkyl group,
(2) when $R_5$ is

$R_2$ is an alkyl group and $R_6$ is a hydrogen atom or an alkyl group,
(3) when $R_6$ is

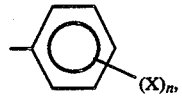

$R_2$ is an optionally substituted ($C_1$–$C_6$) alkyl or ($C_3$–$C_6$) alkenyl group and $R_5$ is a hydrogen atom, a ($C_1$–$C_6$) alkyl group or a halogen atom, and
(4) when $R_2$ and $R_6$ are both independently

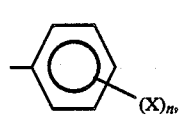

$R_5$ is a hydrogen atom or an alkyl group; Y is a hydrogen atom or an alkyl group; X is a hydrogen atom, a halogen atom, a trihalomethyl group, a ($C_1$–$C_6$) alkyl group, a nitro group, a cyano group or a ($C_1$–$C_6$) alkoxy group; n is an integer from 1 to 3; and the agronomically acceptable alkali metal or acid addition salts thereof. These compounds are useful as chemical hybridization agents for monocotyledonous crops and are especially effective in wheat, corn, barley, rice, rye, triticale, forage crops and the like.

Those compounds which are highly potent chemical gametocides and which produce a high percentage of male sterility without affecting female fertility of cereal grain and forage crops are especially useful as chemical hybridization agents according to the invention. As will be seen in the examples which follow, some of the compounds, particularly at higher application rates, exhibit diminished female fertility along with high male sterility. The latter group of compounds nonetheless have utility for producing new plant hybrids. Although some of the compounds may exhibit some phytotoxicity, the compounds are still useful for the purpose of producing new plant hybrids. In addition to utility as chemical hybridization agents, the compounds of the invention are also useful as chemical gametocides in the agricultural production of ergot.

DETAILED DESCRIPTION OF THE INVENTION

This invention relates to N-alkyl-2-aryl-4-oxonicotinates, N-alkyl-5-aryl-4-oxonicotinates, N-alkyl-6-aryl-4-oxonicotinates, and N-alkyl-2,6-diaryl-4-oxonicotinates and their use as plant hybridization agents in cereal grain and forage crops, especially in wheat, barley and corn.

A. N-alkyl-2-aryl-4-oxonicotinates

In one preferred aspect, this invention relates to compounds of the formula:

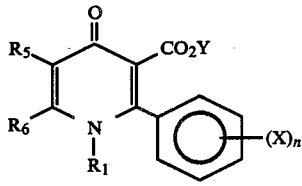

(II)

By the term "optionally substituted alkyl or alkenyl group" as utilized in the present specification and claims is meant a straight or branched chain alkyl or alkenyl group which may be substituted with a hydroxy group, a carboxy group, an aryl group or an aryl group substituted with up to two substituents selected from halogen, methyl, ethyl, methoxy, ethoxy, trifluoromethyl, nitro or cyano.

Since the compounds of the present invention possess both acidic and basic functional groups, the term "agronomically acceptable salts" as utilized in the present specification and claims is meant to include salts of the carboxyl group such as lithium, sodium, potassium, ammonium and the like as well as acid addition salts such as hydrochloride, hydrobromide, sulfate, nitrate, perchlorate, acetate, oxalate and the like.

Among the preferred compounds of the present invention are compounds of Group A, Formula (II) above, wherein $R_1$ is ($C_1$-$C_6$) alkyl or allyl, $R_5$ is hydrogen, ($C_1$-$C_6$) alkyl or bromine, $R_6$ is ($C_1$-$C_6$) alkyl, Y is hydrogen or a sodium or potassium cation, X is hydrogen or halogen, and n is the integer 1 or 2.

Among the more preferred compounds of the present invention are compounds of Formula (II) wherein $R_1$ is ($C_1$-$C_3$) alkyl, $R_5$ is hydrogen, $R_6$ is ($C_1$-$C_3$) alkyl, Y is hydrogen or a sodium or potassium cation, X is hydrogen, chlorine or fluorine and n is the integer 1 or 2.

Among the most preferred compounds of this invention are compounds of Formula (II) wherein $R_1$ is a methyl or ethyl group; $R_5$ is a hydrogen atom; $R_6$ is a methyl group; and Y is a sodium or potassium cation and the agronomically acceptable acid addition salts thereof.

Typical compounds encompassed by the present invention include:
1,6-dimethyl-2-phenyl-4-oxonicotinic acid
1-ethyl-6-methyl-2-phenyl-4-oxonicotinic acid
1,5,6-trimethyl-2-phenyl-4-oxonicotinic acid
1,6-diethyl-2-phenyl-4-oxonicotinic acid
6-ethyl-1-methyl-2-phenyl-4-oxonicotinic acid
1-methyl-2-phenyl-6-propyl-4-oxonicotinic acid
5-bromo-1,6-dimethyl-2-phenyl-4-oxonicotinic acid
1-allyl-6-methyl-2-phenyl-4-oxonicotinic acid
1,6-dimethyl-2-(4-chlorophenyl)-4-oxonicotinic acid
1-ethyl-6-methyl-2-(4-chlorophenyl)-4-oxonicotinic acid
1-ethyl-5,6-dimethyl-2-(4-chlorophenyl)-4-oxonicotinic acid
1,6-diethyl-2-(4-chlorophenyl)-4-oxonicotinic acid
6-ethyl-1-methyl-2-(4-chlorophenyl)-4-oxonicotinic acid
5-bromo-1-ethyl-6-methyl-2-(4-chlorophenyl)-4-oxonicotinic acid
1-allyl-6-methyl-2-(4-chlorophenyl)-4-oxonicotinic acid
6-methyl-2-(4-chlorophenyl)-1-propyl-4-oxonicotinic acid
1-butyl-6-methyl-2-(4-chlorophenyl)-4-oxonicotinic acid
1,6-dimethyl-2-(3-chlorophenyl)-4-oxonicotinic acid
1-ethyl-6-methyl-2-(3-chlorophenyl)-4-oxonicotinic acid
6-methyl-2-(3-chlorophenyl)-1-propyl-4-oxonicotinic acid
1-ethyl-5,6-dimethyl-2-(3-chlorophenyl)-4-oxonicotinic acid
5-chloro-1-ethyl-6-methyl-2-(3-chlorophenyl)-4-oxonicotinic acid
1-hexyl-6-methyl-2-(3-chlorophenyl)-4-oxonicotinic acid
1-allyl-6-ethyl-2-(3-chlorophenyl)-4-oxonicotinic acid
1,6-diethyl-2-(3-chlorophenyl)-4-oxonicotinic acid
1-ethyl-6-methyl-2-(4-trifluoromethylphenyl)-4-oxonicotinic acid
1-ethyl-6-methyl-2-(4-trifluoromethylphenyl)-4-oxonicotinic acid
1,6-dimethyl-2-(4-fluorophenyl)-4-oxonicotinic acid
1-ethyl-6-methyl-2-(4-fluorophenyl)-4-oxonicotinic acid
1-ethyl-6-methyl-2-(3-fluorophenyl)-4-oxonicotinic acid
1-ethyl-6-methyl-2-(4-bromophenyl)-4-oxonicotinic acid
1,6-dimethyl-2-(3,4-dichlorophenyl)-4-oxonicotinic acid
1-ethyl-6-methyl-2-(3,4-dichlorophenyl)-4-oxonicotinic acid
6-methyl-2-(3,4-dichlorophenyl)-1-propyl-4-oxonicotinic acid
6-methyl-1-pentyl-2-(3,4-dichlorophenyl)-4-oxonicotinic acid
6-ethyl-1-methyl-2-(3,4-dichlorophenyl)-4-oxonicotinic acid
1-ethyl-2-(3,4-dichlorophenyl)-6-propyl-4-oxonicotinic acid
1,5,6-trimethyl-2-(3,4-dichlorophenyl)-4-oxonicotinic acid
5-bromo-1,6-dimethyl-2-(3,4-dichlorophenyl)-4-oxonicotinic acid
1,5-diethyl-6-methyl-2-(3,4-dichlorophenyl)-4-oxonicotinic acid 5-ethyl-1,6-dimethyl-2-(3,4-dichlorophenyl)-4-oxonicotinic acid
1-ethyl-6-methyl-2-(2,4-dichlorophenyl)-4-oxonicotinic acid
1,6-dimethyl-2-(3,5-dichlorophenyl)-4-oxonicotinic acid
1-ethyl-6-methyl-2-(4-methylphenyl)-4-oxonicotinic acid
6-butyl-1-methyl-2-(4-methylphenyl)-4-oxonicotinic acid and the agronomically acceptable salts thereof.

The compounds of Group A of the present invention can be prepared by various synthetic routes found in the art. In particular, the compounds of the present invention can be prepared by the reaction of a suitably substituted 4-hydroxy-2-pyrone of the formula:

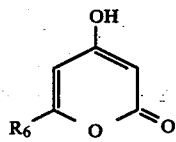
(III)

wherein $R^6$ is as defined above with a benzoylhalide of the formula:

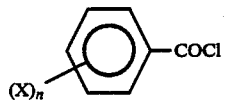
(IV)

wherein X is as defined above in the presence of an acid scavenger such as pyridine, triethylamine and the like, at temperatures from about 0° to about 10° C. to form a 4-benzoyloxy-2-pyrone of the formula:

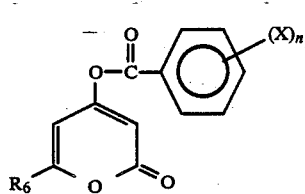
(V)

wherein $R_6$ and X and n are as defined above.

This reaction is discussed in E. Marcus, J. F. Stephen, J. K. Chan, *Journal of Heterocyclic Chemistry*, p. 13, 1966. This benzoate can undergo a Fries-type rearrangement with anhydrous aluminum chloride at elevated temperatures to give the product of the formula:

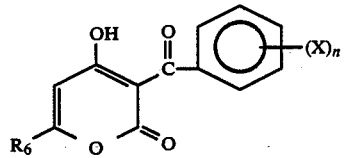
(VI)

as discussed in the E. Marcus, et al. reference, ibid. The benzoylpyrone of the formula (V) above can then be reacted with a suitable alcohol (ROH) in the presence of a similarly substituted trialkylorthoformate $(RO)_3CH$ utilizing an acid catalyst selected from the group consisting of sulfuric, hydrochloric, trifluoroacetic, acetic, hydrobromic, and the like, at temperatures from about 0° to about 200° C. to form the 3-carboxy-4-pyrone of the formula:

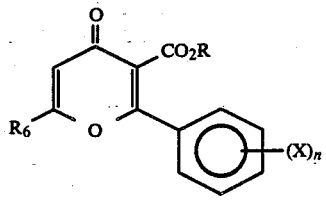
(VII)

The 3-carboxy-4-pyrone esters of formula (VII) can be reacted with any suitably substituted amine of the formula:

$R_1—NH_2$ (VIII)

to yield a 1-alkyl-2-aryl-4-oxonicotinate ester of formula (IX) where $R_5$ is hydrogen.

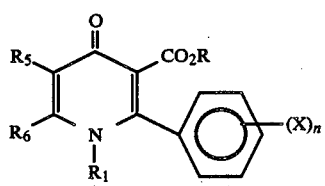
(IX)

This reaction is generally carried out in an inert solvent, such as toluene, xylene, benzene, chloroform, methylene chloride, methanol, ethanol or the like, at room temperature or at a temperature at which the water formed during the reaction can be removed by azeotropic distillation, using about 0 to 5% by weight of an acid catalyst such as p-toluenesulfonic acid, hydrochloric acid, sulfuric acid, methanesulfonic acid, or the like. The free acid, its salts, amides, and other esters can then be prepared by conventional techniques.

The reaction of 3-carboxy-4-pyrone ester of formula (VII) with excess amine of formula (VIII) in methanol or ethanol at 0°-50° C. also results in the formation of a 2:1 amine:pyrone adduct of formula (X).

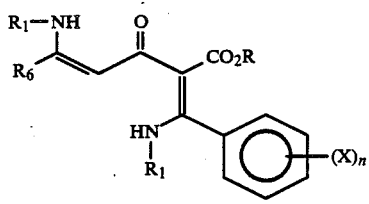
(X)

Compound (X) can be converted to (IX) by hydrolysis with dilute aqueous acids such as hydrochloric, sulfuric, trifluoroacetic or methanesulfonic at 0°-50° C. Alternately, 2:1 adduct (X) can be alkylated with an alkyl halide in an inert solvent such as methylene chloride, benzene, tetrahydrofuran, diethyl ether and the like to provide a material of formula (XI) wherein $R_5$ is an alkyl group;

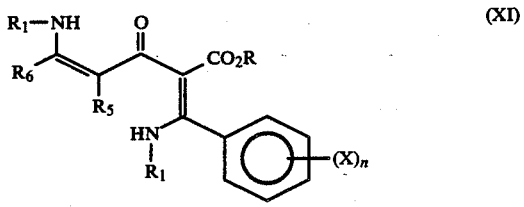

This compound can be hydrolyzed in aqueous acids at 0°-50° C. as described above to yield the corresponding 1,5-dialkyl-2-aryl-4-oxonicotinate ester of formula (IX) where $R_5$ is alkyl. The oxonicotinic acid esters produced in the above reactions can be converted to the free acids by hydrolysis with a strong base such as sodium hydroxide or potassium hydroxide and the like followed by neutralization with a strong acid.

Another route to the preparation of the compounds according to Formula (II) wherein $R_1$ and X are as defined above, $R_5$ is hydrogen and $R_6$ is methyl is depicted in the following reaction sequence:

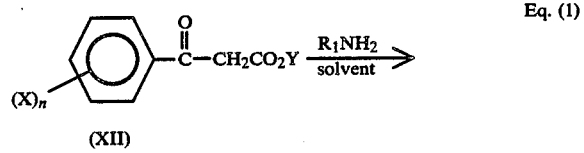

wherein Y is a $(C_1-C_6)$ alkyl group.

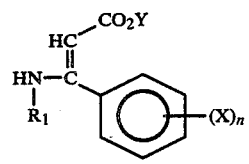

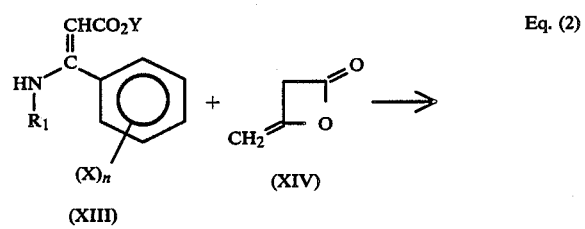

wherein Y is a $(C_1-C_6)$ alkyl group.

Formula XV $\xrightarrow{\text{1. saponification}}{\text{2. H}^+}$ Eq. (3)

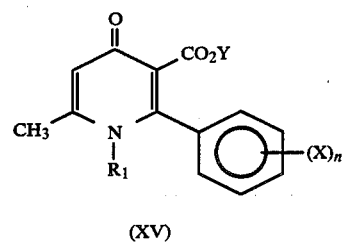

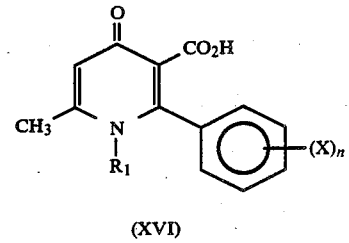

In the above reaction sequence the solvents for Eq. (1) can be selected from methanol, ethanol, water and the like and the reaction is run at temperatures from about 20° to about 100° C. In Eq. (2), the inert solvent is selected from ethers, methylene chloride, aromatic hydrocarbons, acetone, acetonitrile and the like and the reaction is run at temperatures from about 10° to about 150° C. In Eq. (3) the saponification reaction is run at 10°-100° C. with a strong base, such as sodium or potassium hydroxide, and the alkali salt is converted to the free acid via mineral acids such as hydrochloride, sulfuric and the like.

Another route to the compounds of the present invention wherein $R_1$ and $R_6$ are as defined above and $R_5$ is hydrogen or alkyl is shown in equation (4) below.

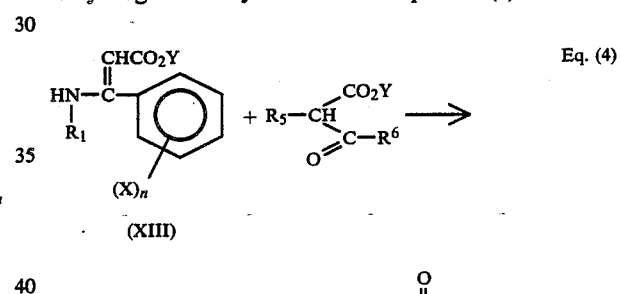

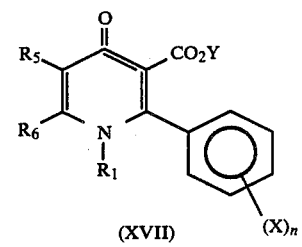

wherein Y is an alkyl group.

In the reaction sequence of Eq. (4) the reaction can be run either neat or in an inert cosolvent optionally in the presence of an acid catalyst such as toluene sulfonic acid, sulfuric acid, acetic acid and the like at temperatures from about 100° C. to about 300° C.

A route to the 5-halo compounds encompassed by the present invention is shown in Eq. (5) below.

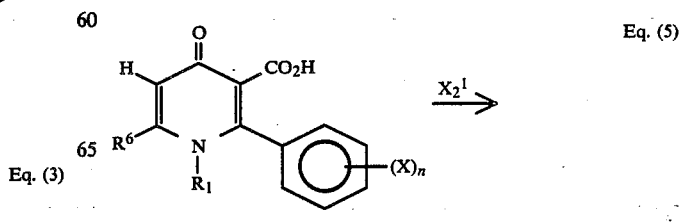

-continued

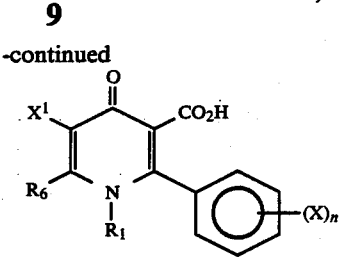

In this reaction sequence any protic solvent such as water, methanol, ethanol and the like can be utilized as the reaction medium and the reaction can be carried out at temperatures from about 10° to about 50° C.

The salts of the oxonicotinic acids of the present invention can be prepared by generally known procedures such as dissolving the acids in a protic solvent such as methanol, ethanol, water and the like and treating them with an equivalent amount of a strong base such as sodium or potassium hydroxide and the like, and recovering the salt either by stripping off the solvent or precipitating the solid out with a diethylether, hexane, benzene and the like.

Table I below is presented to illustrate the more preferred compounds of the present invention. This table and Tables II and III in which the analytical data is presented for these compounds are not to be interpreted in any way as being limits on the breadth and scope of the present invention:

TABLE I

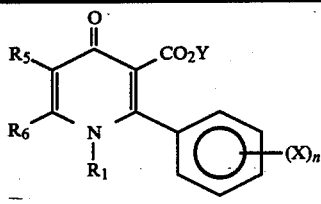

| Example # | $X_{(n)}$ | $R_1$ | $R_5$ | $R_6$ | Y |
|---|---|---|---|---|---|
| 1 | H | $CH_3$ | H | $CH_3$ | $CH_3$ |
| 2 | H | $CH_3$ | H | $CH_3$ | $CH_2CH_3$ |
| 3 | H | $CH_3$ | H | $CH_3$ | $CH_2CH_3 \cdot HCl$ |
| 4 | H | $CH_3$ | H | $CH_3$ | H |
| 4a | H | $CH_3$ | H | $CH_3$ | Na |
| 5 | H | $CH_2CH_3$ | H | $CH_3$ | H |
| 6 | H | $n$-$C_3H_7$ | H | $CH_3$ | H |
| 6a | H | $n$-$C_3H_7$ | H | $CH_3$ | Na |
| 7 | H | $n$-$C_4H_9$ | H | $CH_3$ | H |
| 7a | H | $n$-$C_4H_9$ | H | $CH_3$ | Na |
| 8 | H | $CH_3$ | H | $CH_2CH_3$ | H |
| 8a | H | $CH_3$ | H | $CH_2CH_3$ | Na |
| 9 | H | $CH_3$ | H | $n$-$C_3H_7$ | H |
| 9a | H | $CH_3$ | H | $n$-$C_3H_7$ | Na |
| 10 | H | $CH_2CH_3$ | H | $CH_2CH_3$ | H |
| 10a | H | $CH_2CH_3$ | H | $CH_2CH_3$ | Na |
| 11 | H | $CH_3$ | $CH_3$ | $CH_3$ | H |
| 11a | H | $CH_3$ | $CH_3$ | $CH_3$ | Na |
| 12 | 4-Cl | H | H | $CH_3$ | H |
| 12a | 4-Cl | H | H | $CH_3$ | Na |
| 13 | 4-Cl | $CH_3$ | H | $CH_3$ | H |
| 13a | 4-Cl | $CH_3$ | H | $CH_3$ | Na |
| 14 | 4-Cl | $CH_2CH_3$ | H | $CH_3$ | $CH_3$ |
| 15 | 4-Cl | $CH_2CH_3$ | H | $CH_3$ | $CH_2CH_3$ |
| 16 | 4-Cl | $CH_2CH_3$ | H | $CH_3$ | H |
| 16a | 4-Cl | $CH_2CH_3$ | H | $CH_3$ | Na |
| 17 | 4-Cl | $CH_2CH_3$ | $CH_3$ | $CH_3$ | H |
| 17a | 4-Cl | $CH_2CH_3$ | $CH_3$ | $CH_3$ | Na |
| 18 | 4-Cl | $n$-$C_3H_7$ | H | $CH_3$ | H |
| 18a | 4-Cl | $n$-$C_3H_7$ | H | $CH_3$ | Na |
| 19 | 4-Cl | $CH_2CH_2OH$ | H | $CH_3$ | H |
| 19a | 4-Cl | $CH_2CH_2OH$ | H | $CH_3$ | Na |

TABLE I-continued

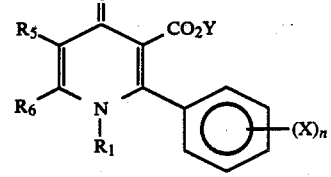

| Example # | $X_{(n)}$ | $R_1$ | $R_5$ | $R_6$ | Y |
|---|---|---|---|---|---|
| 20 | 4-Cl | $CH_2CO_2H$ | H | $CH_3$ | $CH_3$ |
| 20a | 4-Cl | $CH_2CO_2Na$ | H | $CH_3$ | $CH_3$ |
| 21 | 4-Cl | $CH_3CO_2H$ | H | $CH_3$ | H |
| 21a | 4-Cl | $CH_2CO_2Na$ | H | $CH_3$ | Na |
| 22 | 4-Cl | $CH_2CH=CH_2$ | H | $CH_3$ | H |
| 22a | 4-Cl | $CH_2CH=CH_2$ | H | $CH_3$ | Na |
| 23 | 4-Cl | $n$-$C_6H_{13}$ | H | $CH_3$ | H |
| 23a | 4-Cl | $n$-$C_6H_{13}$ | H | $CH_3$ | Na |
| 24 | 4-Cl | $CH_2CH_2Ph$ | H | $CH_3$ | H |
| 24a | 4-Cl | $CH_2CH_2Ph$ | H | $CH_3$ | Na |
| 25 | 4-$CH_3$ | $CH_3$ | H | $CH_3$ | H |
| 25a | 4-$CH_3$ | $CH_3$ | H | $CH_3$ | Na |
| 26 | 4-$CH_3$ | $CH_2CH_3$ | H | $CH_3$ | H |
| 26a | 4-$CH_3$ | $CH_2CH_3$ | H | $CH_3$ | Na |
| 27 | 4-F | $CH_3$ | H | $CH_3$ | H |
| 27a | 4-F | $CH_3$ | H | $CH_3$ | Na |
| 28 | 4-F | $CH_2CH_3$ | H | $CH_3$ | H |
| 28a | 4-F | $CH_2CH_3$ | H | $CH_3$ | Na |
| 29 | 4-F | $n$-$C_3H_7$ | H | $CH_3$ | H |
| 29a | 4-F | $n$-$C_3H_7$ | H | $CH_3$ | Na |
| 30 | 3-Cl | $CH_3$ | H | $CH_3$ | H |
| 30a | 3-Cl | $CH_3$ | H | $CH_3$ | Na |
| 31 | 3-Cl | $CH_2CH_3$ | H | $CH_3$ | $CH_3$ |
| 32 | 3-Cl | $CH_2CH_3$ | H | $CH_3$ | H |
| 32a | 3-Cl | $CH_2CH_3$ | H | $CH_3$ | Na |
| 33 | 3-Cl | $n$-$C_3H_7$ | H | $CH_3$ | H |
| 33a | 3-Cl | $n$-$C_3H_7$ | H | $CH_3$ | Na |
| 34 | 3-Cl | $n$-$C_4H_9$ | H | $CH_3$ | H |
| 34a | 3-Cl | $n$-$C_4H_9$ | H | $CH_3$ | Na |
| 35 | 3-Cl | $CH_2Ph$ | H | $CH_3$ | H |
| 35a | 3-Cl | $CH_2Ph$ | H | $CH_3$ | Na |
| 36 | 3-$CH_3$ | $CH_2CH_3$ | H | $CH_3$ | H |
| 36a | 3-$CH_3$ | $CH_2CH_3$ | H | $CH_3$ | Na |
| 37 | 3-F | $CH_3$ | H | $CH_3$ | H |
| 37a | 3-F | $CH_3$ | H | $CH_3$ | Na |
| 38 | 3-F | $CH_2CH_3$ | H | $CH_3$ | H |
| 38a | 3-F | $CH_2CH_3$ | H | $CH_3$ | Na |
| 39 | 2-Cl | $CH_3$ | H | $CH_3$ | H |
| 39a | 2-Cl | $CH_3$ | H | $CH_3$ | Na |
| 40 | 2-Cl | $CH_3$ | H | $CH_3$ | H |
| 40a | 2-Cl | $CH_2CH_3$ | H | $CH_3$ | Na |
| 41 | 3,4-diCl | H | H | $CH_3$ | $CH_3$ |
| 42 | 3,4-diCl | $CH_3$ | H | $CH_3$ | H |
| 42a | 3,4-diCl | $CH_3$ | H | $CH_3$ | Na |
| 43 | 3,4-diCl | $CH_2CH_3$ | H | $CH_3$ | H |
| 43a | 3,4-diCl | $CH_2CH_3$ | H | $CH_3$ | Na |
| 44 | 3,4-diCl | $n$-$C_3H_7$ | H | $CH_3$ | H |
| 44a | 3,4-diCl | $n$-$C_3H_7$ | H | $CH_3$ | Na |
| 45 | 2,4-diCl | $CH_3$ | H | $CH_3$ | H |
| 45a | 2,4-diCl | $CH_3$ | H | $CH_3$ | Na |
| 46 | 2,4-diCl | $CH_2CH_3$ | H | $CH_3$ | H |
| 46a | 2,4-diCl | $CH_2CH_3$ | H | $CH_3$ | Na |
| 47 | H | $CH_3$ | Br | $CH_3$ | H |
| 47a | H | $CH_3$ | Br | $CH_3$ | Na |

TABLE II

| Example # | mp (°C.) | % C | % H | % N | % X |
|---|---|---|---|---|---|
| 1 | 226–8 | 70.02 | 5.88 | 5.45 | — |
|   |   | 70.35 | 6.01 | 3.60 | — |
| 2 | 244–8 | 70.83 | 6.32 | 5.16 | — |
|   |   | 70.92 | 6.17 | 5.66 | — |
| 3 | 229–32 | 62.44 | 5.89 | 4.55 | — |
|   |   | 62.00 | 5.67 | 4.78 | — |
| 4 | 246–8 | 69.12 | 5.39 | 5.76 | — |
|   |   | 69.05 | 5.66 | 5.80 | — |

TABLE II-continued

| Example # | mp (°C.) | % C | % H | % N | % X |
|---|---|---|---|---|---|
| 4a | a | — | — | — | — |
| 5 | 252–4 | 70.02 | 5.88 | 5.45 | — |
|  |  | 69.63 | 5.76 | 5.64 | — |
| 5a | a | — | — | — | — |
| 6 | 210–2 | 70.83 | 6.32 | 5.16 | — |
|  |  | 70.67 | 5.93 | 5.33 | — |
| 6a | a |  |  |  |  |
| 7 | 165–7 | 71.56 | 6.71 | 4.91 | — |
|  |  | 73.87 | 6.80 | 5.30 | — |
| 7a | a | — | — | — | — |
| 8 | 244–5 | 70.02 | 5.88 | 5.44 | — |
|  |  | 70.15 | 5.65 | 6.07 | — |
| 8a | a | — | — | — | — |
| 9 | 126–8 | 70.83 | 6.32 | 5.16 | — |
|  |  | 70.61 | 6.39 | 5.36 | — |
| 9a | a | — | — | — | — |
| 10 | 187–8 | 70.83 | 6.32 | 5.16 | — |
|  |  | 70.87 | 6.29 | 5.66 | — |
| 10a | a | — | — | — | — |
| 11 | 210–4 | 70.02 | 5.88 | 5.44 | — |
|  |  | 69.92 | 5.96 | 5.96 | — |
| 11a |  |  |  |  |  |
| 12 | 250–1 | 59.31 | 3.82 | 5.31 | 13.45 |
|  |  | 59.05 | 3.77 | 5.38 | 13.46 |
| 12a | a | — | — | — | — |
| 13 | 242–4 | 60.55 | 4.36 | 5.04 | 12.77 |
|  |  | 60.17 | 4.36 | 5.53 | 13.07 |
| 13a | a | — | — | — | — |
| 14 | 217–9 | 62.85 | 5.28 | 4.58 | 11.60 |
|  |  | 62.98 | 5.49 | 4.55 | 11.45 |
| 15 |  |  |  |  |  |
| 16 | 235–7 | 61.75 | 4.84 | 4.80 | 12.16 |
|  |  | 60.50 | 4.75 | 5.75 | 13.66 |
| 16a | a | — | — | — | — |
| 17 | 240–2 | 62.85 | 5.28 | 4.58 | 11.60 |
|  |  | 62.86 | 5.37 | 4.71 | 11.48 |
| 17a | a | — | — | — | — |
| 18 | 213–6 | 62.85 | 5.27 | 4.58 | 11.60 |
|  |  | 62.76 | 5.25 | 5.05 | 11.50 |
| 18a | a | — | — | — | — |
| 19 | 217–20 | 58.54 | 4.59 | 4.55 | 11.52 |
|  |  | 58.31 | 4.52 | 4.75 | 11.91 |
| 19a | a | — | — | — | — |
| 20 | 224 | 57.24 | 4.20 | 4.17 | 10.57 |
|  |  | 57.21 | 4.20 | 4.66 | 10.30 |
| 20a | a | — | — | — | — |
| 21 (dihydrate) | 158–62 | 50.36 | 4.51 | 3.92 | 9.91 |
|  |  | 50.38 | 3.93 | 3.89 | 9.85 |
| 21a | a | — | — | — | — |
| 22 | 219–21 | 63.26 | 4.65 | 4.61 | 11.67 |
|  |  | 63.30 | 4.59 | 5.09 | 11.75 |
| 22a | a | — | — | — | — |
| 23 | 178–9 | 65.60 | 6.38 | 4.03 | 10.19 |
|  |  | 65.84 | 6.66 | 4.29 | 10.22 |
| 23a | a | — | — | — | — |
| 24 | 265 | 68.57 | 4.93 | 3.81 | 9.64 |
|  |  | 68.48 | 4.95 | 4.12 | 9.44 |
| 24a | a | — | — | — | — |
| 25 | 250 | 70.02 | 5.88 | 5.44 | — |
|  |  | 69.92 | 6.03 | 5.46 | — |
| 25a | a | — | — | — | — |
| 26 | 248–9 | 70.83 | 6.31 | 5.16 | — |
|  |  | 70.64 | 6.39 | 5.60 | — |
| 26a | a | — | — | — | — |
| 27 | 263–5 | 64.36 | 4.63 | 5.36 | 7.27 |
|  |  | 64.60 | 4.63 | 5.53 | 7.10 |
| 27a | a | — | — | — | — |
| 28 | 258–60 | 65.44 | 5.13 | 5.09 | 6.90 |
|  |  | 65.60 | 5.26 | 5.24 | 6.80 |
| 28a | a | — | — | — | — |
| 29 | 225–6 | 66.42 | 5.58 | 4.84 | 6.57 |
|  |  | 66.60 | 5.74 | 5.11 | 6.47 |
| 29a | a | — | — | — | — |
| 30 | 248–50 | 60.55 | 4.36 | 5.04 | 12.77 |
|  |  | 60.68 | 4.47 | 5.41 | 12.77 |
| 30a | a | — | — | — | — |
| 31 | 173–5 | 62.85 | 5.28 | 4.58 | 11.60 |
|  |  | 62.88 | 5.54 | 5.06 | 11.80 |
| 32 | 241–4 | 61.75 | 4.84 | 4.80 | 12.16 |
|  |  | 62.01 | 4.83 | 4.97 | 12.25 |
| 32a | a | — | — | — | — |
| 33 | 164–9 | 62.85 | 5.28 | 4.58 | 11.60 |
|  |  | 60.83 | 5.40 | 4.34 | 14.09 |
| 33a | a | — | — | — | — |
| 34 | 174–6 | 63.85 | 5.67 | 4.38 | 11.09 |
|  |  | 63.65 | 5.86 | 4.41 | 11.19 |
| 34a | a | — | — | — | — |
| 35 | 235–5 | 67.89 | 4.56 | 3.96 | 10.02 |
|  |  | 68.14 | 4.54 | 4.06 | 10.18 |
| 35a | a | — | — | — | — |
| 36 | 183 | 70.83 | 6.31 | 5.16 | — |
|  |  | 70.29 | 6.38 | 5.24 | — |
| 36a | a | — | — | — | — |
| 37 | 243–4 | 64.36 | 4.63 | 5.36 | 7.27 |
|  |  | 64.34 | 4.96 | 5.40 | 7.07 |
| 37a | a | — | — | — | — |
| 38 | 226–7 | 65.44 | 5.13 | 5.09 | 6.90 |
|  |  | 65.43 | 5.24 | 5.10 | 6.93 |
| 38a | a | — | — | — | — |
| 39 | 221–3 | 60.55 | 4.36 | 5.04 | 12.77 |
|  |  | 60.53 | 4.30 | 4.95 | 17.62 |
| 40 | 212–5 | 61.75 | 4.84 | 4.80 | 12.16 |
|  |  | 61.94 | 4.85 | 4.93 | 12.06 |
| 40a | a | — | — | — | — |
| 41 | 245–9 | 53.87 | 3.55 | 4.49 | 22.72 |
|  |  | 53.79 | 3.57 | 4.95 | 23.09 |
| 42 | 246–9 | 53.87 | 3.55 | 4.49 | 22.72 |
|  |  | 53.40 | 3.55 | 4.42 | 23.10 |
| 42a | a | — | — | — | — |
| 43 | 238–9 | 55.23 | 4.02 | 4.30 | 21.74 |
|  |  | 54.68 | 3.90 | 4.06 | 23.06 |
| 43a | a | — | — | — | — |
| 44 | 232–3 | 56.48 | 4.44 | 4.19 | 20.84 |
|  |  | 56.69 | 4.47 | 4.29 | 20.49 |
| 44a | a | — | — | — | — |
| 45 | 232–4 | 53.87 | 3.55 | 4.49 | 27.72 |
|  |  | 53.96 | 3.57 | 4.88 | 22.69 |
| 45a | a | — | — | — | — |
| 46 | 195 | 55.23 | 4.02 | 4.30 | 21.72 |
|  |  | 55.82 | 4.02 | 4.72 | 21.73 |
| 46a | a | — | — | — | — |
| 47 | 252–3 | 52.19 | 3.76 | 4.35 | 24.81 |
|  |  | 51.72 | 3.67 | 4.26 | 24.78 |
| 47a | a | — | — | — | — | a no melting point taken. Too glassy.

TABLE III

NMR DATA

| Example | Solvent | NMR-CHEMICAL SHIFT* |
|---|---|---|
| 1 | CDCl$_3$ | 3H at 2.4 ppm(s): 3H at 3.3 pm(s); 3H at 3.45 (s); 1H at 6.4 ppm(s); 5H at 7.5 ppm(m) |
| 2 | — | — |
| 3 | — | — |
| 4 | CF$_3$CO$_2$H | 3H at 2.9 ppm(s); 3H at 3.8 ppm(s); 6H at 7.6 ppm(m) |
| 4a | CF$_3$CO$_2$H | 3H at 1.4 ppm(t); 3H at 2.9 ppm(s); 2H at 4.5 ppm(q); 6H at 7.7 ppm(m) |
| 5 |  |  |
| 6 | — | — |
| 6a |  |  |
| 7 | CDCl$_3$ | 7H at 0.7–17 ppm(m); 3H at 2.5 ppm(s); 2H at 3.7 ppm(m); 1H at 6.8 ppm(s); 5H at 7.5 ppm(m) |
| 7a | — | — |
| 8a | — | — |
| 9 | — | — |
| 9a | — | — |
| 10 | — | — |
| 10a | — | — |
| 11 | — | — |
| 11a | — | — |
| 12 | CF$_3$CO$_2$H | 3H at 2.9 ppm(s); 5H at 7.6 ppm(m) |
| 12a |  |  |
| 13 | CDCl$_3$+dmso-d$_6$ | 3H at 2.5 ppm(s); 3H at 3.3 ppm(s); 1H at 6.8 ppm(s); 4H at 7.5 ppm(q) |
| 13a | CDCl$_3$ |  |
| 14 | CDCl$_3$ | 3H at 1.1 ppm(t); 3H at 2.4 ppm(s); 3H at 3.5 ppm(s); 2H at 3.8 ppm(q); |

TABLE III-continued
NMR DATA

| Example | Solvent | NMR-CHEMICAL SHIFT* |
|---|---|---|
| 15 | — | 1H at 6.5 ppm(s) 4H at 7.5 ppm(q) |
| 16 | CDCl3 | 3H at 1.2 ppm(t); 3H at 2.75 ppm(s); 2H at 4.2 ppm(q); 1H at 6.9 ppm(s); 4H at 7.9 ppm (m) |
| 16a | D2O | 3H at 0.8 ppm(t); 3H at 2.3 ppm(s); 2H at 3.7 ppm(q); 1H at 6.6 ppm(s), 4H at 7.6 ppm(s) |
| 17 | DMSO-d6 | 3H at 1.1 ppm(t); 3H at 2.2 ppm(s); 3H at 2.6 ppm(s); 2H at 3.9 ppm(q); 4H at 7.6 ppm(q) |
| 17a | — | — |
| 18 | — | — |
| 18a | — | — |
| 19 | DMSO-d6 | 3H at 2.6 ppm(s); 2H at 3.4 ppm(m); 2H at 3.9 ppm(m); 1H at 6.9 ppm(s); 4H at 7.4 ppm(q) |
| 19a | — | — |
| 20 | DMSO-d6 | 3H at 2.3 ppm(s); 3H at 3.4 ppm(s); 2H at 4.5 ppm(s); 1H at 6.4 ppm(s); 4H at 7.6 ppm(q) |
| 20a | — | — |
| 21 | — | — |
| 21a | — | — |
| 22 | — | — |
| 22a | — | — |
| 23 | — | — |
| 23a | — | — |
| 24 | — | — |
| 24a | — | — |
| 25 | CDCl3+dmso-d6 | 3H at 2.4 ppm(s); 3H at 2.5 ppm(s); 3H at 3.3 ppm(s); 1H at 6.8 ppm(s); 4H at 7.3 ppm(q) |
| 25a | — | — |
| 26 | — | — |
| 26a | — | — |
| 27 | CF3CO2H | 3H at 2.8 ppm(s); 3H at 3.8 ppm(s); 5H at 7.5 ppm(m) |
| 27a | — | — |
| 28 | — | — |
| 28a | — | — |
| 29 | — | — |
| 29a | — | — |
| 30 | — | — |
| 30a | — | — |
| 31 | CDCl3 | 3H at 1.1 ppm(t); 3H at 2.4 ppm(s); 3H at 3.5 ppm(s); 2H at 3.8 ppm (q); 1H at 6.4 ppm(s); 4H at 7.5 ppm(m) |
| 32 | — | — |
| 32a | — | — |
| 33 | CDCl3 | 3H at 0.7 ppm(t); 2H at 1.5 ppm(m); 3H at 2.6 ppm(s); 2H at 3.6 ppm(q); 1H at 6.8 ppm(s); 4H at 7.5 ppm(m) |
| 33a | — | — |
| 34 | CDCl3 | 7H at 0.7-1.7 ppm(m); 3H at 2.5 ppm(s); 2H at 3.7 ppm(m); 1H at 6.8 ppm(s); 4H at 7.5 ppm(m) |
| 34a | — | — |
| 35 | — | — |
| 35a | — | — |
| 36 | CDCl3 | 3H at 1.1 ppm(t); 3H at 2.4 ppm(S); 3H at 2.6 ppm(s); 2H at 3.9 ppm(q); 1H at 6.8 ppm(s); 4H at 7.4 ppm(m) |
| 36a | — | — |
| 37 | — | — |
| 37a | — | — |
| 38 | DMSO-d6 | 3H at 1.1 ppm(t); 3H at 2.6 ppm(s); 2H at 3.8 ppm(q); 1H at 6.9 ppm(s); 4H at 7.5 ppm(m) |
| 38a | — | — |
| 39 | — | — |
| 39a | — | — |
| 40 | — | — |
| 40a | — | — |
| 41 | CF3CO2H | 3H at 2.8 ppm(s); 3H at 3.9 ppm(s); 4H at 7.6 ppm(m) |
| 42 | — | — |
| 42a | — | — |
| 43 | — | — |
| 43a | — | — |
| 44 | — | — |
| 44a | — | — |
| 45 | CF3CO2H | 3H at 2.9 ppm(s); 3H at 3.9 ppm(s); 4H at 7.7 ppm(m) |
| 45a | — | — |
| 46 | CDCl3 | 3H at 1.2 ppm(t); 3H at 2.6 ppm(s); 2H at 3.8 ppm(q); 1H at 6.8 ppm(s); 3H at 7.5 ppm(m) |
| 46a | — | — |
| 47 | — | — |
| 47a | — | — |

*s = singlet
t = triplet
q = quartet
m = multiplet

The following examples are presented to illustrate the methods for preparation of the compounds of the present invention. Again these examples are not to be interpreted as being limits upon the breadth and scope of the present invention.

EXPERIMENTAL

Example #1

Part a

A flask fitted with a reflux condenser and calcium chloride drying tube is charged with 70 ml dry methanol, 7.3 gms of 96% sulfuric acid and 10.15 gms of trimethyl orthoformate. 3-Benzoyl-4-hydroxy-6-methyl-2-pyrone (22 gms) is then added in small portions and the resulting reaction mixture is refluxed for 24 hours. The mixture is cooled and poured into water. Extraction with methylene chloride yields 17.7 gms of crude 3-methoxycarbonyl-6-methyl-2-phenyl-4-pyrone. mp (from methylene chloride/ether = 101-2.5

Part b 3.8 gms of 3-methoxycarbonyl-6-methyl-2-phenyl-4-pyrone, 33.3 ml of methanol, 13.3 mls of 40% aqueous methylamine and 2 mls of glacial acetic acid are mixed in a stoppered flask at room temperature and stored for 18 hours. The reaction mixture is then poured into approximately 100 ml of water and the pH is adjusted to 5 (addition of dilute HCl). Extraction with methylene chloride (3×50 mls) and evaporation of the organic solvent yields 3.0 gms of methyl 1,6-dimethyl-2-phenyl-4-oxonicotinate as a crystalline solid. mp (methylene chloride/ether)=226-8.

Example #2

10.25 gms of ethyl beta-methylaminocinnamate, 9.4 gms of technical grade diketene and 25 mls dry methylene chloride are mixed in a flask fitted with a calcium chloride drying tube. The reaction mixture is stored at room temperature for 117 hours. Approximately 75 ml of dry ether is added and the resulting crystalline solid is filtered to yield 8.5 gms of ethyl 1,6-dimethyl-2-phenyl-4-oxonicotinate. mp (toluene)=244-8.

Example #4

6.0 gms of crude methyl 1,6-dimethyl-2-phenyl-4-oxonicotinate is suspended in 66 gms of 5% aqueous sodium hydroxide solution. The reaction mixture is heated on a steambath (85°) for two hours. The resulting homogeneous solution is cooled and acidified with dilute HCl. The resulting solid is collected by filtration yielding 4.9 gms of 1,6-dimethyl-2-phenyl-4-oxonicotinic acid. mp (acetonitrile/methylene chloride)=246-9 (dec.).

Example 4a 1.69 gms of 1,6-dimethyl-2-phenyl-4-oxonicotinic acid is suspended in approximately 50 mls of methanol. NaOH pellets (0.305 gms) are added with stirring. After both the acid and the sodium hydroxide dissolve the solution is evaporated to dryness in vacuo. Sodium 1,6-dimethyl-2-phenyl-4-oxonicotinate is then isolated as a glossy, somewhat hydroscopic solid. Yield=1.6 gms.

Example 8

Part a 12 gms of ethyl beta-methylaminocinnamate, 18 gms of ethyl propionylacetate and 100 mgs of toluenesulfonic acid monohydrate are added to a 50 ml 3-neck flask fitted with a nitrogen inlet, magnetic stirring bar, thermometer and a short-path distillation head (with receiver). The reaction mixture is heated to 170°-5° under a slow stream of dry nitrogen. Ethanol and water are collected in the distillation receiver. After four hours the reaction mixture is cooled and poured into a large volume of ether (150 mls). A pink solid forms which is collected by filtration to yield 4.1 gms of ethyl 6-ethyl-1-methyl-2-phenyl-4-oxonicotinate. mp (EtOAC)=210°-2°.

Part b 2.2 gms of ethyl 6-ethyl-1-methyl-2-phenyl-4-oxonicotinate is suspended in 35 ml of 5% aqueous sodium hydroxide solution. The resulting suspension is heated on a steambath for 4 hours, cooled and acidified with dilute HCl to yield 2.0 gms of 6-ethyl-1-methyl-2-phenyl-4-oxonicotinic acid. mp ($CH_3CN$)=244°-5°.

Example 11

Part a 12.0 gms of ethyl beta-methylaminocinnamate, 18 gms of ethyl 2-methylacetoacetate and 100 mgs toluenesulfonic acid monohydrate is mixed in a 50 ml 3-neck flask filled with a nitrogen inlet, magnetic stirring bar, thermometer and a short-path distillation head (with receiver). The reaction mixture is heated (170-5) for seven hours under a gentle stream of nitrogen. Ethanol and water are collected in the distillation receiver. The reaction mixture is cooled and poured into 100 ml of dry ether. Ethyl 1,5,6-trimethyl-2-phenyl-4-oxonicotinate forms as a brownish precipitate. Yield=1.03 gms.

Part b 1.03 gms of crude ethyl 1,5,6-trimethyl-2-phenyl-4-oxonicotinate is suspended in 20 mls of warm (85°) 5% aqueous NaOH solution for 4 hours. Acidification with dilute hydrochloric acid yields 0.8 gms of 1,5,6-trimethyl-2-phenyl-4-oxonicotinate mp ($CH_3CN$)=210°-4°.

Example 14

Part a

A 5000 ml 3-neck flask is fitted with a $N_2$ inlet, magnetic stirring bar, thermometer and a Dean-Stark trap with condenser. 2300 mls of dry methanol is added to the flask along with 244 gms of 96% $H_2SO_4$ and 352 gms of trimethyl orthoformate. 173 gms of 3-(4'-chlorobenzoyl)-4-hydroxy-6-methyl-2-pyrone is added and the reaction mixture is gently brought to reflux. The most volatile by-product of the reaction (methyl formate) is condensed and collected in the Dean-Stark trap. After 28½ hours of reflux the reaction mixture is cooled to room temperature and poured into 6000 mls of brine. The resulting suspension is extracted with methylene chloride (6×250 mls). Evaporation of the solvent yields 153 gms of 3-methoxycarbonyl-6-methyl-2-(4'-chlorophenyl)-4-pyrone. mp (methylene chloride/ether)=131-2.

Part b

A 1000 ml flask is fitted with a magnetic stirring bar and a sidearm addition funnel. 500 mls of methanol, 30 mls of glacial acetic acid and 60 gms of 3-methoxycarbonyl-6-methyl-2-(4'-chlorophenyl)-4-pyrone are added. 120 mls of 70% aqueous ethylamine is placed in the addition funnel and added very slowly (4 hr. addition time). 50 mls of water is then added followed by 100 mls of concentrated HCl (cooling required). The reaction mixture is allowed to stand undisturbed for 30 minutes. The bulk of the methanol is then removed in vacuo leaving 46.1 gms of methyl 1-ethyl-6-methyl-2-(4'-chlorophenyl)-4-oxonicotinate. mp (methylene chloride/ether)=217°-219° C.

Example 16

46.1 gms of crude methyl 1-ethyl-6-methyl-2-(4'-chlorophenyl)-4-oxonicotinate is suspended in 600 mls of 5% aqueous NaOH solution and warmed to 80°-85°. After 1½ hours at this temperature the reaction mixture is cooled and acidified with dilute HCl. The resulting solid precipitate is collected by filtration, yielding 42 gms of 1-ethyl-6-methyl-2-(4'-chlorophenyl)-4-oxonicotinic acid, mp (methylene chloride/ether)=235°-7°.

Example 15

4.64 gms of ethyl beta-ethylamino-4-chlorocinnamate, 4.61 gms of technical grade diketene and 15 mls of methylene chloride are mixed in a flask fitted with a calcium chloride drying tube. The mixture is maintained at room temperature for 137 hours. The methylene chloride is removed in vacuo and the residue triturated with ether to yield 3.2 gms of crude ethyl 1-ethyl-6-methyl-2-(4'-chlorophenyl)-4-oxonicotinate. mp (215-17).

Example 15

6 gms of ethyl beta-ethylamino-4-chlorocinnamate and 12 gms of ethyl acetoacetate is mixed in a 50 ml 3-neck flask fitted with a $N_2$-inlet, magnetic stirring bar, thermometer and a short-path distillation head (with receiver). The reaction mixture is heated (170°) for 10 hours. Ethanol and water is collected in the distillation receiver. The reaction mixture is cooled and triturated with ethyl acetate/ether to yield 2.52 gms of ethyl 1-ethyl-6-methyl-2-(4'-chlorophenyl)-4-oxonicotinate.

Example 17

Part a 69 gms of 3-methoxycarbonyl-6-methyl-2-(4'-chlorophenyl)-4-pyrone, 500 mls of methanol, 90 mls of water and 30 mls of glacial acetic acid are mixed in a 1000 ml flask fitted with a magnetic stirring bar and a sidearm addition funnel. 120 mls of 70% aqueous ethylamine is added over the course of one hour. The reaction mixture is then allowed to stand at room temperature for one hour, neutralized with dilute HCl and extracted with methylene chloride (2×250 mls, 2×150 mls). The organic extracts are evaporated and the residue triturated with ether. The first crop of crystals is pure methyl 1-ethyl-6-methyl-2-(4'-chlorophenyl)-4-oxonicotinate (33.1 gms). The solid that forms upon further concentration of the mother liquor is pure alpha-[3-ethylamino-2-butenoyl]-beta-ethylamino-4-chlorocinnamate. Yield=11 gms. mp=144 (ether).

Part b 7 gms of alpha-[3-ethylamino-2-butenoyl]-beta-ethylamino-4-chlorocinnamate, 5.7 gms methyl iodide, and 20 mls of methylene chloride are mixed in a sealed flask, and stored for 22 hours at room temperature. The contents of the flask are then poured into a separatory funnel and washed with water. Evaporation of the organic layer leaves 9.4 gms of oil which is dissolved in 80 mls of tetrahydrofan. 60 mls of water and 4 mls of trifluoroacetic acid is then added and the mixture is allowed to remain at room temperature for two hours. Subsequent dilution with water and extraction with methylene chloride provides 8.0 gms of crude 4-oxonicotinate ester. This material is then heated in 80 mls of 5% aqueous sodium hydroxide solution (85°, 2 hrs.) and acidified to yield 2.3 gms of 1-ethyl-5,6-dimethyl-2-(4'-chlorophenyl)-4-oxonicotinic acid. mp=240°-242° C. (acetonitrile).

Example 20

8.7 gms of 3-methoxycarbonyl-6-methyl-2-(4'-chlorophenyl)-4-pyrone is suspended in 100 mls of methanol and 10 mls of water. In a separate flask, 7.01 gms of glycine, 3.12 gms of sodium hydroxide and 50 mls of methanol are mixed and allowed to stir for 30 minutes to form a solution of the sodium salt of glycine. This solution is then added to the pyrone suspension with stirring. The resulting reaction mixture is allowed to stir at room temperature for five hours. 80 mls of water and 10 mls of concentrated hydrochloric acid is added. A precipitate forms within a few minutes. This is collected by filtration to yield 7.0 gms of methyl 1-carboxymethyl-6-methyl-2-(4'-chlorophenyl)-4-oxonicotinate. mp (methanol/water)=224.

Example 21

4.0 gms of 1-carboxymethyl-6-methyl-2-(4'-chlorophenyl)-4-oxonicotinate is suspended in 40 gms of 5% aqueous sodium hydroxide solution and heated at 80°-85° for two hours. The reaction mixture is cooled and acidified to give a white precipitate. This precipitate is collected by filtration to yield 2.9 gms of 1-carboxymethyl-6-methyl-2-(4'-chlorophenyl)-4-oxonicotinic acid. mp (CH₃CN)=158-62.

Example 22

Part a 10 gms of 3-methoxycarbonyl-6-methyl-2-(4'-chlorophenyl)-4-pyrone, 1.65 gms glacial acetic acid and 100 mls of methanol are mixed in 500 ml flask fitted with a magnetic stirring bar and sidearm additionl funnel. 6.15 gms of allylamine are slowly added (one hour addition time). Three hours later 20 mls of water and 8 mls of concentrate HCl are added. This reaction mixture is allowed to stand at room temperature for one hour, then is poured into 400 mls of water and extracted with methylene chloride (2×100 mls). Removal of the solvent yields 10 gms of crude methyl 1-allyl-6-methyl-2-(4'-chlorophenyl)-4-oxonicotinate.

Part b

The crude oxonicotinate ester isolated above is suspended in 80 mls of 5% aqueous sodium hydroxide solution and heated at 85° for 2½ hours. Acidification of this reaction mixture with dilute HCl provides 6.7 gms of 1-allyl-6-methyl-2-(4'-chlorophenyl)-4-oxonicotinic acid. mp (acetonitrile)=219°-21°.

Example 47

6.0 gms of 1,6-dimethyl-2-phenyl-4-oxonicotinic acid is suspended in 200 mls of methanol. 1.0 gms of sodium hydroxide is added. As soon as the acid dissolves a solution of 5.52 gms of Br₂ in 50 mls of methanol is slowly added with stirring. The pH of the reaction mixture is maintained at 8-9 by the addition of extra sodium hydroxide as required. A precipitate of 3,5-dibromo-1,6-dimethyl-2-phenyl-pyrid-4-one forms. This material is collected by filtration and discarded. Acidification of the clear filtrate yields 3.4 gms of 5-bromo-1,6-dimethyl-2-phenyl-4-oxonicotinic acid as a white solid. mp=252°-3° (acetonitrile).

B. N-alkyl-6-aryl-4-oxonicotinates

In another preferred aspect, this invention relates to compounds of the formula:

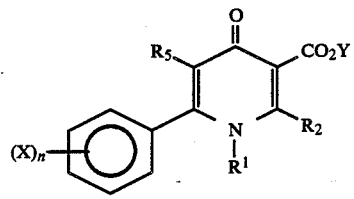

(XVIII)

wherein $R_1$ and $R_2$ are, independently, an optionally substituted ($C_1$-$C_6$) alkyl or a ($C_3$-$C_6$) alkenyl group; $R_5$ is hydrogen or halogen; Y is a hydrogen atom or a ($C_1$-$C_6$) alkyl group; X is a hydrogen atom, a halogen atom, a trihalomethyl group, a ($C_1$-$C_6$) alkyl group, a nitro group, a cyano group or a ($C_1$-$C_6$) alkoxy group; n is an integer from 1 to 3; and the agronomically acceptable salts thereof.

Among the preferred compounds of the present invention are compounds of Group B, Formula XVIII, wherein $R_1$ and $R_2$ are, independently ($C_1$-$C_6$) alkyl, ($C_1$-$C_4$) haloalkyl, alkoxy ($C_1$-$C_4$) alkyl ($C_1$-$C_4$), aryl ($C_1$-$C_4$) alkyl ($C_1$-$C_4$) or ($C_3$-$C_6$) alkenyl; Y is a hydrogen, ($C_1$-$C_6$) alkyl, or an alkali or alkaline earth metal cation; $R_5$ is hydrogen or halogen; X is hydrogen, halogen, trihalomethyl, ($C_1$-$C_6$) alkyl, ($C_1$-$C_6$) alkoxy, nitro or cyano; and n is an integer from 1 to 3.

Among the more preferred compounds of the present invention are compounds of Group B, Formula XVIII, wherein $R_1$ and $R_2$ are, independently, ($C_1$-$C_4$) alkyl; Y is hydrogen, $CH_3$, $C_2H_5$, Na or K; $R_5$ is hydrogen or bromine; X is hydrogen, methoxy, methyl, trifluoromethyl, iodine, bromine, chlorine or fluorine and n is an integer from 1 to 3.

Among the most preferred compounds of this invention are compounds of Group B, Formula XVIII, where $R_1$ is a methyl or ethyl group; $R_2$ is a methyl, ethyl, or n-propyl group; $R_5$ is hydrogen or a bromine atom; X is hydrogen, methyl, trifluoromethyl; or bromine, chlorine or fluorine atom and n is 1 or 2; and Y is a sodium or potassium cation, hydrogen, or a methyl or ethyl group; and the agronomically acceptable acid addition salts thereof.

Typical compounds encompassed by the present invention include:

1,2-dimethyl-6-(3-fluorophenyl)-4-oxonicotinic acid;
2-n-butyl-1-ethyl-6-(4-methoxyphenyl)-4-oxonicotinic acid;
1-allyl-6-phenyl-2-n-propyl-4-oxonicotinic acid;
1-(3-chloropropyl)-2-methyl-6-phenyl-4-oxonicotinic acid;
1-(2-ethoxy methyl)-2-methyl-6-phenyl-4-oxonicotinic acid;
1-benzyl-2-n-propyl-6-(4-trifluoromethylphenyl)-4-oxonicotinic acid;
1,2-di-n-propyl-6-(4-fluorophenyl)-4-oxonicotinic acid;
1,2-dimethyl-6-phenyl-4-thioxonicotinic acid;
6-(4-chlorophenyl)-1,2-diethyl-4-oxonicotinic acid;
5-bromo-6-(4-chlorophenyl)-1,2-dimethyl-4-oxonicotinic acid;
6-(4-chlorophenyl)-1,2,5-trimethyl-4-oxonicotinic acid;
1,5-dimethyl-6-(4-fluorophenyl)-2-n-propyl-4-oxonicotinic acid;
1,2-dimethyl-6-(1-naphthyl)-4-oxonicotinic acid;
6-(3,5-dichlorophenyl)-1-methyl-2-n-propyl-4-oxonicotinic acid;
5-(4-chlorophenyl)-1-i-propyl-2-methyl-4-oxonicotinic acid;
2-i-propyl-1-methyl-6-phenyl-4-oxonicotinic acid and metal salts thereof;
ethyl 1,2-dimethyl-6-(4-fluorophenyl)-4-oxonicotinate
methyl 6-(4-chlorophenyl)-1-ethyl-2-methyl-4-oxonicotinate
n-propyl 1-methyl-6-phenyl-2-n-propyl-4-oxonicotinate
i-propyl 1-allyl-6-(4-bromophenyl)-2-methyl-4-oxonicotinate
n-butyl 6-(3-chlorophenyl)-1-ethyl-2-n-propyl-4-oxonicotinate
n-hexyl 1,2-dimethyl-6-(4-iodophenyl)-4-oxonicotinate
and the agronomically acceptable salts thereof.

The Group B compounds of the present invention are prepared by various synthetic routes found in the art. In particular, the Group B compounds of the present invention can be prepared by the following reaction sequence:

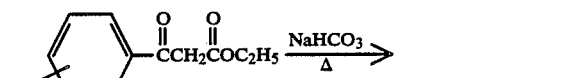

(XIX)

-continued

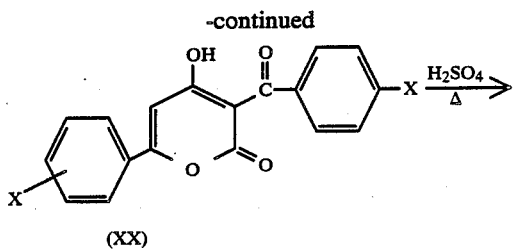

(XX)

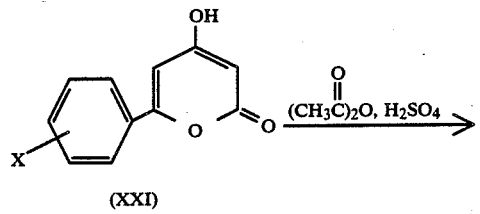

(XXI)

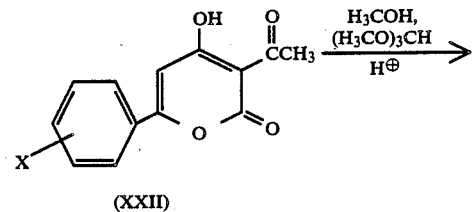

(XXII)

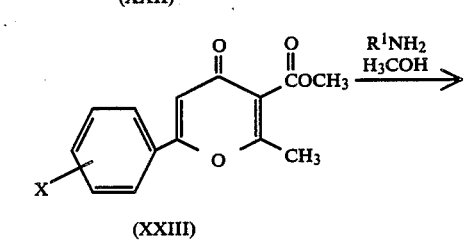

(XXIII)

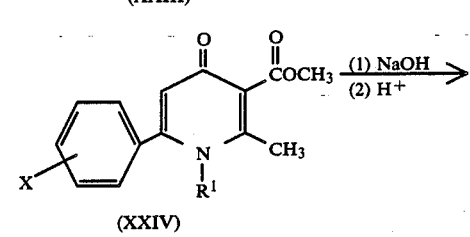

(XXIV)

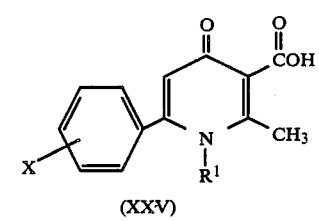

(XXV)

Alternatively, the Group B compounds can be prepared by the following reaction sequence:

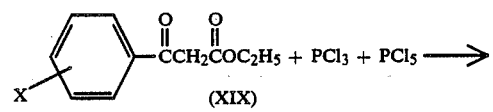

(XIX)

-continued

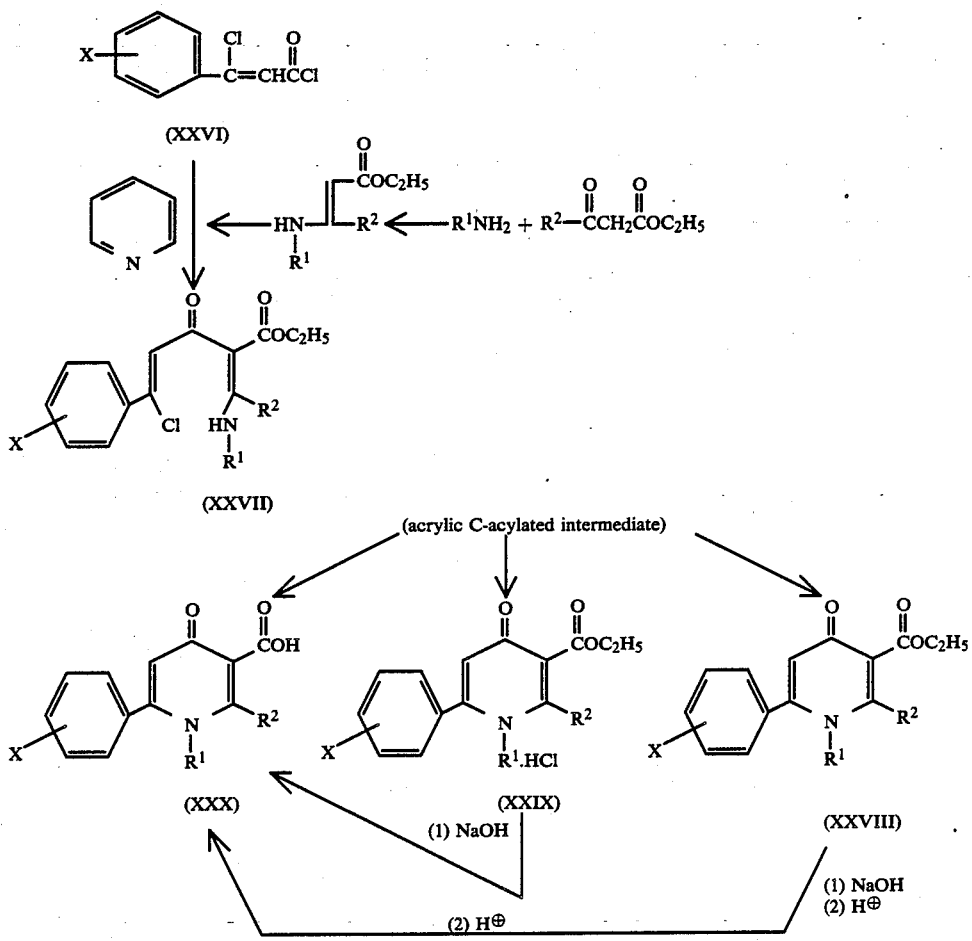

In the latter reaction sequence, the cyclization step yielded one or more of the pyridones, XXVIII, XXIX and XXX. In general, a pyrolysis (neat) of the acyclic C-acylated intermediate (XXVII) yielded the oxonicotinic acid (XXX) directly. Cyclization of the acyclic intermediate (XXVII) in aprotic solvents at lower temperatures gave varied results depending on reaction conditions and the X, $R_1$ and $R_2$ substituent effects. In some cases, mixtures of products were obtained (ester, ester hydrochloride and acid), in other cases only one of the products was isolated.

The salts of the Group B oxonicotinic acids of the present invention can be prepared by generally known procedures such as dissolving the acids in a proctic solvent such as methanol, ethanol, water and the like and treating them with an equivalent amount of a strong base such as sodium or potassium hydroxide and the like, and recovering the salt either by stripping off the solvent or precipitating the solid out with a diethylether, hexane, benzene and the like.

Table IV below is presented to illustrate the more preferred compounds of the present invention. This table and Table II in which the analytical data is presented for these compounds are not to be interpreted in any way as being limits on the breadth and scope of the present invention:

TABLE IV
LIST OF COMPOUNDS

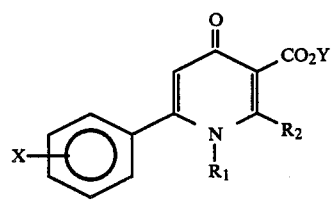
(XXVIII)

| Example | X | $R_1$ | $R_2$ | Y | % Yield (from acid chloride) | Recryst. Solvent |
|---|---|---|---|---|---|---|
| 48 | H | Me | Me | Et | 37[a] | MDC/ether |
| 49 | H | Me | Me | Et-HCl | 37[a] | None |
|  | H | Me | Me | H | 35[a] | MDC/ether |

TABLE IV-continued
LIST OF COMPOUNDS

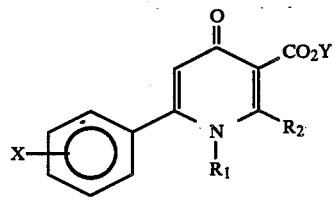

(XXVIII)

| Example | X | R₁ | R₂ | Y | % Yield (from acid chloride) | Recryst. Solvent |
|---|---|---|---|---|---|---|
| 50 | H | Me | Me | Na | — | — |
|  | H | Et | Me | H | 15[b] | CH₃CN |
| 51 | H | Et | Me | Na | — | — |
|  | H | Pr | Me | H | 23[a] | CH₃CN |
| 52 | H | Pr | Me | Na | — | — |
|  | H | n-Hexyl | Me | H | 10[a] | methyl cyclohexane |
| 53 | H | n-Hexyl | Me | Na | — | — |
|  | H | Me | n-Pr | H | 30[a] | MDC/ether |
| 54 | H | Me | n-Pr | Na | — | — |
|  | 4-CH₃ | Me | Me | H | 20[b] | CH₃CN |
| 55 | 4-CH₃ | Me | Me | Na | — | — |
|  | 4-F | Me | Me | H | 16[b] | CH₃CN |
| 56 | 4-F | Me | Me | Na | — | — |
| 57 | 4-Cl | Me | Me | C₂H₅ | 37[a] | Toluene |
|  | 4-Cl | Me | Me | H | 25[a] | — |
| 58 | 4-Cl | Me | Me | Na | — | — |
|  | 4-Cl | Et | Me | H | 17[a] | — |
| 59 | 4-Cl | Et | Me | Na | — | — |
|  | 4-Cl | n-Hexyl | Me | H | 7[a] | Methyl cyclohexane |
| 60 | 4-Cl | n-Hexyl | Me | Na | — | — |
|  | 3-CH₃ | Me | Me | H | 23[a] | — |
| 61 (HCl salt) | 3-CH₃ | Me | Me | Na | — | — |
|  | 3,4-diCl | CH₃ | CH₃ | H | 35[a] | — |
| 62 | 3,4-diCl | CH₃ | CH₃ | Na | — | — |
|  | 4-I | CH₃ | CH₃ | H | 34[a] | — |
| 63 | 4-I | CH₃ | CH₃ | Na | — | — |
|  | 3-Cl | CH₃ | CH₃ | H | 21[a] | — |
| 64 | 3-Cl | CH₃ | CH₃ | Na | — | — |
|  | 4-OCH₃ | CH₃ | CH₃ | H | 4.2[a] | — |
| 65 | 4-OCH₃ | CH₃ | CH₃ | Na | — | — |
| 66 (HCl salt) | 4-Br | H | CH₃ | Et | 24[a] | Methyl cyclohexane |
|  | 4-Br | CH₃ | CH₃ | H | 44[a] | — |
| 67 | 4-Br | CH₃ | CH₃ | Na | — | — |
| 68 | 4-Cl | CH₂-φ | CH₃ | Et | 9.3[a] | — |
|  | 4-Cl | CH₂-φ | CH₃ | H | 6[a] | — |
| 69 | 4-Cl | CH₂-φ | CH₃ | Na | — | — |
| 70 (HCl salt) | 4-CF₃ | CH₃ | CH₃ | Et | 35[a] | — |
|  | 4-CF₃ | CH₃ | CH₃ | H | 29[a] | — |
| 71 | 4-CF₃ | CH₃ | CH₃ | Na | — | — |
| 72 (HCl salt) | 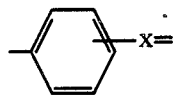 | CH₃ | CH₃ | Et | 38.5[a] | — |
|  | 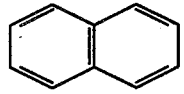 |  |  |  |  |  |
|  | 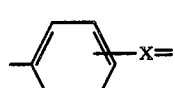 | CH₃ | CH₃ | H | 35[a] | — |
|  | 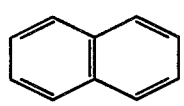 |  |  |  |  |  |
| 73 | 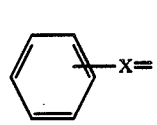 | CH₃ | CH₃ | Na | — | — |

TABLE IV-continued
LIST OF COMPOUNDS

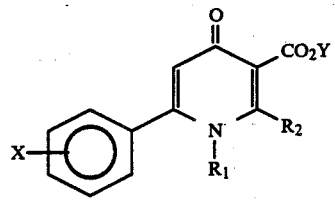

(XXVIII)

| Example | X | R₁ | R₂ | Y | % Yield (from acid chloride) | Recryst. Solvent |
|---|---|---|---|---|---|---|

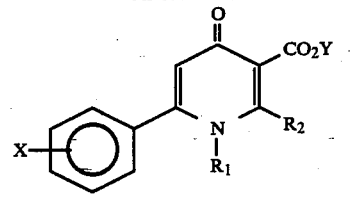

| Example | X | R₁ | R₂ | Y | % Yield (from acid chloride) | Recryst. Solvent |
|---|---|---|---|---|---|---|
| 74 (Hcl) (salt) | 4-Cl | CH₃ | CH₃ | Et | 44[a] | — |
| 75 (Hcl) (salt) | 4-Cl | CH₃ | n-C₃H₇ | Et | 23[a] | — |
|  | 4-Cl | CH₃ | n-C₃H₇ | H | 17[a] | — |
| 76 | 4-Cl | CH₃ | n-C₃H₇ | Na | — | — |
|  | H | C₂H₇ | n-C₃H₇ | H | 7.5[a] | — |
| 77 | H | C₂H₅ | n-C₃H₇ | Na | — | — |
| (5-Br) | H | CH₃ | CH₃ | H | — | — |
| 78 (5-Br) | H | CH₃ | CH₃ | Na | — | — |

[a]Xylene method
[b]Direct pyrolysis

TABLE V
ANALYTICAL DATA

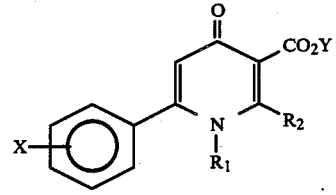

(XXVIII)

| Example # | mp (°C.) | Elemental Analysis[a] %C | %H | %N | %X |
|---|---|---|---|---|---|
| 48 | 154 | 70.83 | 6.32 | 5.16 | — |
|  |  | 71.03 | 6.39 | 5.33 | — |
| 49 | 211-3 | — | — | — | — |
|  | 220-2.5 | 69.12 | 5.39 | 5.76 | — |
|  |  | 68.65 | 5.34 | 6.10 | — |
| 50 | — | — | — | — | — |
|  | 216-7 | 70.02 | 5.88 | 5.45 | — |
|  |  | 70.26 | 5.93 | 5.69 | — |
| 51 | — | — | — | — | — |
|  | 210-11 | 70.83 | 6.32 | 5.16 | — |
|  |  | 70.40 | 6.29 | 5.60 | — |
| 52 | — | — | — | — | — |
|  | 129-30 | 72.82 | 7.40 | 4.47 | — |
|  |  | 72.33 | 7.35 | 4.73 | — |
| 53 | — | — | — | — | — |
|  | 150 | 70.83 | 6.32 | 5.16 | — |
|  |  | 70.41 | 6.23 | 5.19 | — |
| 54 | — | — | — | — | — |
|  | 213-5 | 70.02 | 5.88 | 5.44 | — |
|  |  | 69.38 | 5.69 | 5.20 | — |
| 55 | — | — | — | — | — |
|  | 141-2 | 64.36 | 4.63 | 5.36 | 7.27 |
|  |  | 63.16 | 4.35 | 6.14 | 6.94 |
| 56 | — | — | — | — | — |
| 57 | 198 dec | 62.85 | 5.28 | 4.58 | — |
|  |  | 62.82 | 5.31 | 4.66 | — |
|  | 236-238 dec | 60.55 | 4.36 | 5.04 | — |
|  |  | 60.33 | 4.34 | 5.18 | — |
|  | 212-214 dec | 61.75 | 4.84 | 4.80 | — |
|  |  | 61.11 | 4.61 | 5.17 | — |
| 58 | — | — | — | — | — |
| 59 |  |  |  |  |  |
|  | 127-129 | 65.60 | 6.38 | 4.03 | — |

TABLE V-continued
ANALYTICAL DATA (XXVIII)

| Example # | mp (°C.) | %C | %H | %N | %X |
|---|---|---|---|---|---|
|  |  | 65.78 | 6.54 | 4.21 | — |
| 60 | — | — | — | — | — |
|  | 218-220 dec | 70.02 | 5.88 | 5.44 | — |
|  |  | 69.75 | 5.96 | 5.62 | — |
| 61 | — | — | — | — | — |
|  | 271-2 dec | 45.86 | 3.85 | 3.82 | — |
|  |  | 44.82 | 3.22 | 4.06 | — |
| 62 | 297-9 dec | — | — | — | — |
|  | 283-4 dec | 45.55 | 3.28 | 3.79 | — |
|  |  | 45.63 | 3.37 | 3.79 | — |
| 63 | >300 | — | — | — | — |
|  | 265-6 dec | — | — | — | — |
| 64 | — | — | — | — | — |
|  | 226-236 dec | 65.92 | 5.53 | 5.13 | — |
|  |  | 65.29 | 5.34 | 5.68 | — |
| 65 | — | — | — | — | — |
| 66 | 114 | 48.34 | 4.06 | 3.76 | — |
|  |  | 48.45 | 4.04 | 3.68 | — |
|  | 269-271 dec | 52.19 | 3.76 | 4.35 | — |
|  |  | 52.04 | 3.69 | 4.28 | — |
| 67 | 294-6 dec | — | — | — | — |

| Example # | Recryst. Solvent | mp (°C.) | Elemental Analysis[a] %C | %H | %N | %X |
|---|---|---|---|---|---|---|
| 68 | Toluene | 201-2.5 | 69.20 | 5.28 | 3.67 | — |
|  |  |  | 68.93 | 5.29 | 3.54 | — |
|  | — | 169-173 | 67.89 | 4.56 | 3.96 | — |
|  |  |  | 67.83 | 4.50 | 4.25 | — |
| 69 | — | — | — | — | — | — |

TABLE V-continued

ANALYTICAL DATA (XXVIII)

$$\text{structure: X-phenyl-dihydropyridine with C=O, CO}_2\text{Y, N-R}_1, \text{R}_2$$

| # | | mp | C | H | N | other |
|---|---|---|---|---|---|---|
| 70 | — | 212–214 dec | 54.33 | 4.53 | 3.73 | — |
| | | | 53.92 | 4.65 | 4.01 | — |
| | — | 220–222 dec | 57.88 | 3.89 | 4.50 | — |
| | | | 58.07 | 3.88 | 5.38 | — |
| 71 | — | >310 | — | — | — | — |
| | | | — | — | — | — |
| 72 | — | 212–214 dec | 67.13 | 5.63 | 3.91 | — |
| | | | 67.20 | 5.59 | 3.40 | — |
| | — | 260–3 dec | 73.70 | 5.15 | 4.78 | — |
| | | | 73.34 | 5.14 | 4.76 | — |
| 73 | — | 225–235 dec | — | — | — | — |
| | | | — | — | — | X = Cl |
| 74 | — | 213–215 dec | 56.15 | 5.07 | 4.09 | 20.72 |
| | | | 55.79 | 4.95 | 4.62 | 20.34 |
| 75 | — | 200–2 dec | Poor elemental analysis | | | |
| | — | 184–187 | 62.85 | 5.28 | 4.58 | — |
| | | | 62.00 | 5.27 | 4.89 | — |
| 76 | — | 168–210 dec | — | — | — | — |
| | — | 121–3 dec | 71.56 | 6.71 | 4.91 | — |
| | | | 71.67 | 6.76 | 5.29 | — |
| 77 | —· | 80–100 | — | — | — | — |
| | | | — | — | — | — |
| | H₃CCN | 257–8 | 52.19 | 3.75 | 4.35 | Br 24.81 |
| | | | 52.55 | 3.76 | 4.36 | Br 25.18 |
| 78 | — | — | — | — | — | — |
| | | | — | — | — | — |

[a]Generally the elemental analysis for the Na salts were either not performed or gave poor results due to the hygroscopic nature of the results.

The following examples are presented to illustrate the methods for preparation of the compounds of the present invention. Again these examples are not to be interpreted as being limits upon the breadth and scope of the present invention.

β-Chlorocinnamoyl chloride

A solution of 60 g (0.312 mol) ethyl benzoyl acetate in 96 ml (150 g) of phosphorous trichloride is added dropwise to 150 g (0.72 mol) of phosphorous pentachloride under nitrogen. The suspension that forms is cautiously brought to reflux temperature (HCl evolution observed) and is refluxed and stirred for 2–2½ hrs. The solution that forms is stripped of phosphorous trichloride and phosphorous oxychloride at atmospheric pressure (76°–82° C.). The pot residue is distilled at 97°–108° C./0.75 mm to give 54 g (86% yield) of product as an isomeric mixture.

β-Chloro(4-chloro)cinnamoylchloride

A solution of 22.67 g (0.1 mol) ethyl (4-chlorobenzoyl) acetate in 70 ml of phosphorous trichloride is added dropwise to 52 g (0.25 mol) of phosphorous pentachloride under nitrogen (HCl evolution observed). The suspension that forms is stored at room temperature for ½ hr. and at reflux temperature for 2½ hrs. The solution that forms is stripped of phosphorous trichloride, phosphorous oxychloride and phosphorous pentachloride at 80°–90° C. (pot temperature)/ambient pressure, 90°–110° C. (pot temperature)/40 mm and 90°–130° (pot temperature)/0.15 mm. A yield of 23.35 g (99%) of crude product is obtained as the pot residue;

Ethyl β-methylamino crotonate 186 g (1.43 mol) of ethyl acetoacetate is added dropwise over a period of 10 min. to a solution of 450 ml. of methylamine (40% in water) in 150 ml. of water (exotherm from room temperature to 56° C. observed). The mixture is stirred at room temperature for 2 hrs. and is extracted with chloroform. The chloroform extract is washed with water, dried over magnesium sulfate and concentrated in vacuo. The residue oil is vacuum distilled at 76°–83° C./0.1 mm to afford 143.6 g (70% yield) of yellow oil.

Ethyl 3-methylamino-2-hexeneoate

A solution of 31.64 g (0.2 mol) ethyl butyryl acetate and 5 ml. of ethanol is added dropwise over a period of 5 min. to a solution of 38.7 g (0.6 mol) ethylamine (70% in water) and 50 ml of water (exotherm from 28° C. to 33° C. observed). The mixture is stirred at room temperature for 18 hrs. and is extracted with three 100 ml portions of methylene dichloride (MDC). The methylene dichloride extract is dried over magnesium sulfate and concentrated in vacuo to afford 30.7 g (83% yield) of product, a colorless oil.

Example 48

Ethyl 1,2-dimethyl-6-phenyl-4-oxonicotinate 2.0 g (0.0065 mol.) of ethyl 1,2-dimethyl-6-phenyl-4-oxonicotinate hydrochloride (see Example 49 below) is dissolved in water and treated with dilute sodium hydroxide (pH adjusted to about 8). The precipitate formed is isolated by vacuum filtration to afford 1.9 g of product, mp 154° C. (MDC/ether recrystallization).

Example 49

Ethyl 1,2-dimethyl-6-phenyl-4-oxonicotinate Hydrochloride 9.2 g (0.046 mol.) of β-chlorocinnamoyl chloride (isomer mixture) dissolved in 75 ml of methylene dichloride is added dropwise to a solution of 6.6 g (0.046 mol) of ethyl β-methylaminocrotonate and 7.4 g (0.0937 mol) of pyridine in 100 ml of methylene dichloride under nitrogen (5 min. addition time, slight exotherm from 25° to 35° C.). The reaction mixture is allowed to stand for 1½ hrs. The methylene dichloride layer is isolated and passed through a 2 inch column of silica gel. The column is eluted with an additional 200 ml of methylene dichloride and the light yellow colored eluate is concentrated in vacuo to yield 15 g of ethyl 2-(3-phenyl-3-chloro) acrylyl-3-methylamino crotonate, an oil.

15 g (0.0488 mol) of ethyl 2-(3-phenyl-3-chloro) acrylyl-3-methyl aminocrotonate is suspended in 150 ml of xylene and refluxed for 3 hrs. The reaction mixture is cooled and the suspension is vacuum filtered. The filter cake is dried to afford 5.7 g (38% yield) of product, mp 211°–213° C.

Example 50

Sodium 1,2-dimethyl-6-phenyl-4-oxonicotinate 42 g (0.1366 mol) of ethyl 2-(3-phenyl-3-chloro) acrylyl-3-methyl aminocrotonate is placed in a flask and heated to 140° C. under nitrogen (nitrogen sparge started at this time). The pot temperature was slowly raised to 157° C. over a period of 40 min. The reaction mixture was cooled and extracted into 5% aqueous sodium hydroxide. Acidification of the basic extracts provided 10 g (30% yield) of 1,2-dimethyl-6-phenyl-4-oxonicotinic acid, mp 220°-225° C. (MDC/ether).

15 g (0.01617 mol) of 1,2-dimethyl-6-phenyl-4-oxonicotinic acid is suspended in 200 ml of methanol and to it there is added 2.71 g (0.0678 mol) of sodium hydroxide pellets. The solution formed is concentrated in vacuo to afford 15 g (92% yield) of product.

Example 54

Sodium 1-methyl-6-phenyl-2-propyl-4-oxonicotinate

A solution of 11.4 g (0.057 mol) β-chlorocinnamoyl chloride and 75 ml of methylene dichloride is added over a period of 20 min. to a solution of 8.6 g (0.054 mol) ethyl 3-methylamino-2-hexenoate, 9.0 g (0.114 mol) pyridine and 100 ml of methylene dichloride under nitrogen (slight exotherm from 25°-36° C.). The mixture is allowed to stand at room temperature for 1½ hrs. and is washed with water. The methylene dichloride solution is passed through a 2 inch column of silica gel and is concentrated in vacuo to afford 13 g of ethyl (3-phenyl-3-chloro)acrylyl-3-methylamino-2-hexeneoate, an oil.

13 g (0.0387 mol) of ethyl (3-phenyl-3-chloro) acrylyl-3-methyl-amino-2-hexeneoate is dissolved in 200 ml of xylene and is refluxed and stirred for 4 hrs. The solution is washed with 30 ml of 6N hydrochloric acid. The aqueous washings are neutralized and the precipitate formed is isolated to afford 4.5 g of ethyl 1-methyl-6-phenyl-2-propyl-4-oxonicotinate.

4.5 g (0.015 mol) of ethyl 1-methyl-6-phenyl-2-propyl-4-oxonicotinate is suspended in 60 g of 5% sodium hydroxide in a 1:1 mixture of methanol and water. The mixture is heated at 85° C. and stirred for 2½ hrs. The solution formed is acidified and the suspension formed is vacuum filtered. The filter cake is dried to afford 2.7 g of 1-methyl-6-phenyl-2-propyl-4-oxonicotinic acid, mp 150° C. (MDC/ether). An additional 0.5 g of 1-methyl-6-phenyl-2-propyl-4-oxonicotinic acid is obtained by extraction of the xylene solution with 30 ml of 1% sodium hydroxide and acidification of the basic extract.

2.1 g (0.0067 mol) of 1-methyl-6-phenyl-2-propyl-4-oxonicotinic acid is suspended in 50 ml of methanol and to it there is added 0.295 g (0.0074 mol) of sodium hydroxide pellets. The solution is concentrated in vacuo to afford 1.9 g (97% yield) of product.

Example 57

Ethyl 6-(4-chlorophenyl)-1,2-dimethyl-4-oxonicotinate

A solution of 10 g (0.0425 ml) β-chloro(4-chloro) cinnamoyl chloride in 50 ml of methylene dichloride is added dropwise over a 10 min. period to a solution of 6.08 g (0.0425 mol) ethyl β-methylaminocrotonate, 6.72 g (0.085 mol) of pyridine and 200 ml of methylene dichloride (slight exotherm from 25° to 34° C.). The mixture is stirred at room temperature for 18 hrs. and is washed with water. The methylene dichloride solution is vacuum filtered through 25 g of silica gel and the filtrate is concentrated in vacuo to afford 12.55 g of ethyl [3-(4-chlorophenyl)-3-chloro] acrylyl-3-methylamino-crotonate, an oil.

A solution of 12.55 g (0.037 mol) ethyl [3-(4-chlorophenyl)-3-chloro] acrylyl-3-methylamino crotonate in 50 ml of xylene is refluxed and stirred for 2½ hrs. under nitrogen. The suspension formed is vacuum filtered to afford 6.5 g (52% yield) of ethyl 6-(4-chlorophenyl)-1,2-dimethyl-4-oxonicotinate hydrochloride (Example 27).

A suspension of 6.5 g (0.019 mol) ethyl 6-(4-chlorophenyl)-1,2-dimethyl-4-oxonicotinate hydrochloride in 150 ml of water is treated with sodium hydroxide (pH adjusted to about 8). The suspension formed is vacuum filtered and the filter cake is washed with water and dried to afford 4.9 g (43.3% yield) of product, a white solid, mp 198° C. dec (Toluene).

Example 58

Sodium 6-(4-Chlorophenyl)-1,2-dimethyl-4-oxonicotinate 1.5 g (0.019 mol) of 50% aqueous sodium hydroxide is added to a suspension of 2.9 g (0.0095 mol) ethyl 6-(4-chlorophenyl)-1,2-dimethyl-4-oxonicotinate in 75 ml of water. The mixture is refluxed and stirred for 15 min. and cooled to room temperature. The solution is extracted with methylene dichloride and the aqueous solution is acidified to pH 1 with 12N hydrochloric acid. The suspension formed is vacuum filtered and the filter cake is dried to afford 1.8 g (68% yield) of 6-(4-chlorophenyl)-1,2-dimethyl-4-oxonicotinic acid, mp 236°-238° C. dec.

0.52 g (0.0065 mol) of 50% aqueous sodium hydroxide is added to a suspension of 1.8 g (0.0065 mol) 6-(4-chlorophenyl)-1,2-dimethyl-4-oxonicotinic acid in 35 ml of methanol. The solution formed is allowed to stand at room temperature for 1 hr. and then is concentrated in vacuo. The concentrate is washed with two (25 ml) portions of diethyl ether and dried to afford 1.7 g (87% yield) of product.

Example 67

Sodium 6-(4-Bromophenyl)-1,2-dimethyl-4-oxonicotinate

A solution of 12 g (0.043 mol) β-chloro(4-bromo) cinnamoyl chloride in 25 ml of methylene dichloride is added dropwise over a 3 min. period to a solution of 6.15 g (0.043 mol.) ethyl β-methylamino crotonate, 6.8 g (0.086 mol) of pyridine and 200 ml of methylene dichloride (slight exotherm from 25° C. to 33° C.). The solution is stirred at room temperature for 3 days and is washed with 200 ml of water. The methylene dichloride solution is vacuum filtered through 25 g of silica gel and the filtrate is concentrated in vacuo to afford 11 g (66% yield) of ethyl [3-(4-bromophenyl)-3-chloro] acrylyl-3-methylamino crotonate, a brown oil.

11 g (0.0284 mol) of ethyl [3-(4-bromophenyl)-3-chloro] acrylyl-3-methylamino crotonate is dissolved in 10 ml of toluene and 50 ml of xylene and is refluxed and stirred for 4 hrs. under nitrogen. The suspension formed is stirred at room temperature for 18 hrs. and is vacuum filtered. The filter cake is washed with hexane and dried to afford 5.3 g (48%) of ethyl 6-(4-bromophenyl)-1,2-dimethyl-4-oxonicotinate hydrochloride, mp 206°-210° C. dec.

5.3 g (0.014 mol) of ethyl 6-(4-bromophenyl)-1,2-dimethyl-4-oxonicotinate hydrochloride is suspended in 100 ml of water and to it there is added 5 g (0.0625 mol) of 50% aqueous sodium hydroxide. The mixture is refluxed and stirred for 1 hr. and the solution formed is cooled to room temperature. The solution is extracted with methylenedichloride and the aqueous solution is acidified to pH 1 with 12N hydrochloric acid. The suspension formed is vacuum filtered and the filter cake is washed with water and dried to afford 4 g (89% yield) of 6-(4-bromophenyl)-1,2-dimethyl-4-oxonicotinic acid, mp 269°-271° C. dec.

2 g (0.0062 mol) of 6-(4-bromophenyl)-1,2-dimethyl-4-oxonicotinic acid is suspended in 50 ml of methanol and to it there is added 0.5 g (0.0062 mol) of 50% aqueous sodium hydroxide. The solution formed is allowed to stand at room temperature for 1 hr. and is concentrated in vacuo. The concentrate is washed with 50 ml of diethyl ether and dried to afford 1.9 g (89% yield) of product.

Example 75

Ethyl 6-(4-chlorophenyl)-1-methyl-2-n-propyl-4-oxonicotinate hydrochloride

A solution of 15 g (0.064 mol) β-chloro (4-chloro) cinnamoyl chloride in 50 ml of methlene dichloride is added dropwise over a 3 min. period to a stirred solution of 10.9 g (0.064 mol) ethyl 3-methylamino-2-hexeneoate and 10.1 g (0.128 mol) of pyridine in 200 ml of methylene dichloride (slight exotherm from 25° C. to 34° C.). The solution formed is stirred at room temperature for 18 hrs. and is washed with water. The methylene dichloride solution is vacuum filtered through silica gel and the filtrate is concentrated in vacuo to afford 18.5 g (78% yield) of ethyl [3-(4-chlorophenyl)-3-chloro] acrylyl-3-methylamino-2-hexeneoate, a brown oil.

A solution of 18.5 g (0.05 mol) of ethyl [3-(4-chlorophenyl)-3-chloro] acrylyl-3-methylamino-2-hexeneoate in 15 ml of toluene and 60 ml of xylene is refluxed and stirred for 3 hrs. under nitrogen. The suspension formed is allowed to stand at room temperature for 8 days and is vacuum filtered. The filter cake is washed with toluene and hexane and dried to afford 4.3 g (23% yield) of product, mp 200°–202° C. dec.

Example 76

Sodium 6-(4-chlorophenyl)-1-methyl-2-n-propyl-4-oxonicotinate 4.0 g (0.05 mol) of 50% aqueous sodium hydroxide is added to a suspension of 2.7 g (0.01 mol) ethyl 6-(4-chlorophenyl)-1-methyl-2-n-propyl-4-oxonicotinate hydrochloride in 50 ml of water and 10 ml of ethanol. The mixture is refluxed and stirred for 3 hrs, allowed to stand at room temperature for 18 hrs., refluxed for an additional 1 hr. and cooled to room temperature. The solution formed is extracted with three 50 ml portions of methylene dichloride and the aqueous solution is acidified to pH 1 with 12N hydrochloric acid. The suspension formed is stirred at room temperature for 3 hrs. and is vacuum filtered. The filter cake is dried to afford 1.65 g (54% yield) of 6-(4-chlorophenyl)-1-methyl-2-n-propyl-4-oxonicotinic acid, mp 184°–187° C.

0.42 g (0.0052 mol) of 50% aqueous sodium hydroxide is added to a suspension of 1.6 g (0.0052 mol) 6-(4-chlorophenyl)-1-methyl-2-n-propyl-4-oxonicotinic acid in 25 ml of methanol. The solution formed is allowed to stand at room temperature for 1 hr. and is concentrated in vacuo. The concentrate is dried to afford 1.5 g (88% yield) of product.

Example 78

Sodium 5-Bromo-1,2-dimethyl-6-phenyl-4-oxonicotinate 2.0 g (0.0125 mol) of bromine dissolved in 50 ml. of methanol is added dropwise over a 15 min. period to a solution of 2.7 g (0.00877 mol) ethyl 1,2-dimethyl-6-phenyl-4-oxonicotinate hydrochloride (Example 2) in 15 ml of methanol and 15 ml of water. The suspension formed is vacuum filtered and the filter cake, a yellow solid, is suspended in 60 g of 5% aqueous sodium hydroxide. The mixture is stirred and heated at 85° C. for 2½ hrs. and is acidified with hydrochloric acid. The suspension formed is vacuum filtered to afford 2.4 g (85% yield) of 5-bromo-1,2-dimethyl-6-phenyl-4-oxonicotinic acid, mp 257°–258° C. (CH$_3$CN).

2.1 g (0.065 mol) of 5-bromo-1,2-dimethyl-6-phenyl-4-oxonicotinic acid is suspended in 50 ml of methanol and to it there is added 0.29 g (0.007 mol) of sodium hydroxide pellets. The solution formed is concentrated in vacuo to afford 2.1 g (94% yield) of product.

C. N-alkyl-5-aryl-4-oxonicotinates

In yet another preferred aspect, this invention relates to compounds of the formula:

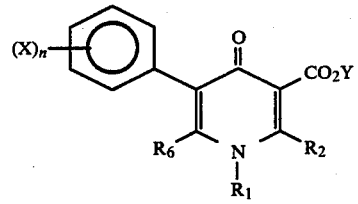

(XXXI)

wherein $R_1$ is an optionally substituted ($C_1$–$C_6$) alkyl group; $R_2$ is a ($C_1$–$C_4$) alkyl group; $R_6$ is a hydrogen atom or a ($C_1$–$C_4$) alkyl group; Y is a hydrogen atom or a ($C_1$–$C_6$) alkyl group or radical; X is a hydrogen atom, a halogen atom, a trihalomethyl group, a ($C_1$–$C_6$) alkyl group, a nitro group, a cyano group or a ($C_1$–$C_4$) alkoxy group; and n is the integer 1 or 2; and the agronomically acceptable salts thereof.

Among the preferred compounds of the present invention are compounds of Group C, Formula (XXXI) wherein $R_1$ and $R_2$ are, independently, ($C_1$–$C_6$) alkyl, ($C_1$–$C_4$) haloalkyl, alkoxy ($C_1$–$C_4$) alkyl ($C_1$–$C_4$), aryl ($C_6$–$C_{10}$) alkyl ($C_1$–$C_4$), or ($C_3$–$C_6$) alkenyl; Y is hydrogen, ($C_1$–$C_6$) alkyl, or an alkali or alkaline earth metal cation; $R_6$ is hydrogen or ($C_1$–$C_4$) alkyl; X is hydrogen, halogen, trihalomethyl, ($C_1$–$C_6$) alkyl, ($C_1$–$C_6$) alkoxy, nitro or cyano; and n is an integer from 1 to 3.

Among the more preferred compounds of the present invention are compounds of Group C, Formula (XXXI) wherein $R_1$ is ($C_1$–$C_6$) alkyl, $R_2$ is ($C_1$–$C_3$) alkyl; $R_6$ is hydrogen or ($C_1$–$C_4$) alkyl, Y is hydrogen, methyl, ethyl or a sodium or potassium cation, X is hydrogen, ($C_1$–$C_6$) alkyl or halogen and n is the integer 1 or 2.

Among the most preferred compounds of this invention are compounds of Group C, Formula (XXXI) wherein $R_1$ is a methyl or ethyl group; $R_2$ is a methyl group; $R_6$ is a hydrogen radical or a methyl group; and Y is ethyl or a sodium or potassium cation; and the agronomically acceptable acid salts thereof.

Typical compounds encompassed by the present invention include:
1,2-dimethyl-5-phenyl-4-oxonicotinic acid
1-ethyl-2-methyl-5-phenyl-4-oxonicotinic acid
1,2,6-trimethyl-5-phenyl-4-oxonicotinic acid
1,2-diethyl-5-phenyl-4-oxonicotinic acid
2-ethyl-1-methyl-5-phenyl-4-oxonicotinic acid
1,2-dimethyl-5-(4-chlorophenyl)-4-oxonicotinic acid
1-ethyl-2-methyl-5-(4-chlorophenyl)-4-oxonicotinic acid 1-ethyl-2,6-dimethyl-5-(4-chlorophenyl)-4-oxonicotinic acid
1,2-diethyl-5-(4-chlorophenyl)-4-oxonicotinic acid
1,2-dimethyl-5-(3-chlorophenyl)-4-oxonicotinic acid
1-ethyl-2-methyl-5-(3-chlorophenyl)-4-oxonicotinic acid
1-ethyl-2,6-dimethyl-5-(3-chlorophenyl)-4-oxonicotinic acid
1-ethyl-2-methyl-5-(4-trifluoromethylphenyl)-4-oxonicotinic acid
1,2-dimethyl-5-(4-fluorophenyl)-4-oxonicotinic acid
1-ethyl-2-methyl-5-(4-fluorophenyl)-4-oxonicotinic acid
1-ethyl-2-methyl-5-(3-fluorophenyl)-4-oxonicotinic acid
1-ethyl-2-methyl-5-(4-bromophenyl)-4-oxonicotinic acid
1,2-dimethyl-5-(3,4-dichlorophenyl)-4-oxonicotinic acid
1-ethyl-2-methyl-5-(3,4-dichlorophenyl)-4-oxonicotinic acid
1,2,6-trimethyl-5-(3,4-dichlorophenyl)-4-oxonicotinic acid
1,2-diethyl-6-methyl-5-(3,4-dichlorophenyl)-4-oxonicotinic acid
2-ethyl-1,6-dimethyl-5-(3,4-dichlorophenyl)-4-oxonicotinic acid
1-ethyl-2-methyl-5-(2,4-dichlorophenyl)-4-oxonicotinic acid
1-ethyl-2-methyl-5-(4-methylphenyl)-4-oxonicotinic acid and the agronomically acceptable salts thereof.

The compounds of the present invention can be prepared by various synthetic routes found in the art.

Tables VI and VII below are presented to illustrate the more preferred compounds of this aspect of the present invention and related compounds and the analytical data for these compounds.

General Syntheses

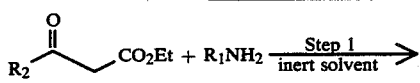

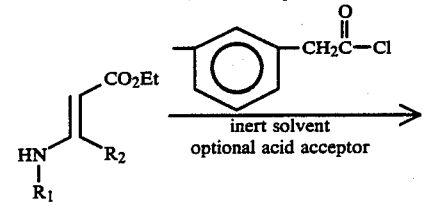

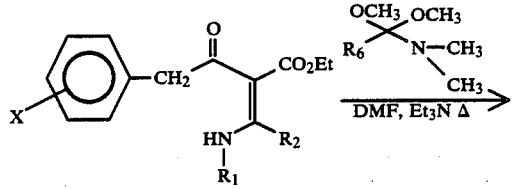

-continued
General Syntheses

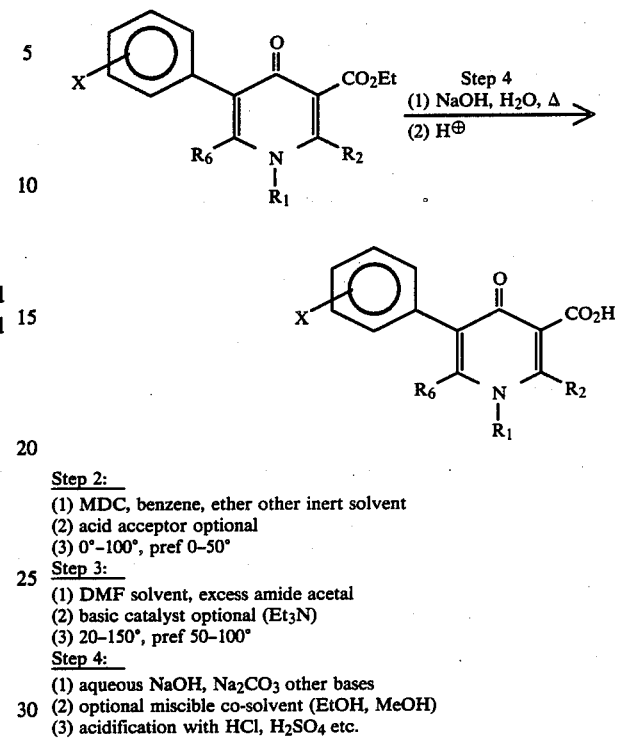

Step 2:
(1) MDC, benzene, ether other inert solvent
(2) acid acceptor optional
(3) 0°-100°, pref 0-50°

Step 3:
(1) DMF solvent, excess amide acetal
(2) basic catalyst optional (Et$_3$N)
(3) 20-150°, pref 50-100°

Step 4:
(1) aqueous NaOH, Na$_2$CO$_3$ other bases
(2) optional miscible co-solvent (EtOH, MeOH)
(3) acidification with HCl, H$_2$SO$_4$ etc.

TABLE VI
List of Group C Compounds

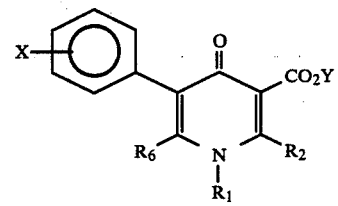

| Example | X$_1$ | R$_1$ | R$_2$ | R$_6$ | Y |
|---|---|---|---|---|---|
| 79 | H | H | H | Me | Et |
| 80 | H | H | H | Me | H |
| 80a | H | H | H | Me | Na |
| 81 | H | Et | H | Me | H |
| 81a | H | Et | H | Me | Na |
| 82 | H | Me | Me | H | Et |
| 83 | H | Me | Me | H | H |
| 83a | H | Me | Me | H | Na |
| 84 | H | Et | Me | H | H |
| 84a | H | Et | Me | H | Na |
| 85 | H | Et | Me | Me | H |
| 85a | H | Et | Me | Me | Na |
| 86 | H | H | Me | Me | H |
| 86a | H | H | Me | Me | Na |
| 87 | 4-Cl | Me | Me | H | Et |
| 88 | 4-Cl | Me | Me | H | H |
| 88a | 4-Cl | Me | Me | H | Na |
| 89 | 4-Cl | Me | Me | Me | H |
| 89a | 4-Cl | Me | Me | Me | Na |
| 90 | 4-Br | Me | Me | H | H |
| 90a | 4-Br | Me | Me | H | Na |
| 91 | 4-Br | Me | n-Pr | H | H |
| 91a | 4-Br | Me | N—Pr | H | Na |
| 92 | 4-Br | n-Hex | Me | H | H |
| 92a | 4-Br | N—Hex | Me | H | Na |
| 93 | 4-Br | Me | Me | Me | H |
| 93a | 4-Br | Me | Me | Me | H |
| 94 | 4-Cl | ∅ | Me | H | H |
| 94a | 4-Cl | ∅ | Me | H | Na |

TABLE VI-continued

List of Group C Compounds

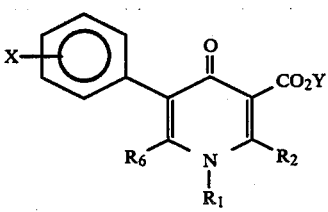

| Example | X₁ | R₁ | R₂ | R₆ | Y |
|---|---|---|---|---|---|
| 95 | H | 4-Fø | Me | H | Et |
| 96 | H | 4-Fø | Me | H | H |
| 96a | H | 4-Fø | Me | H | Na |

TABLE VII

Analytical Data - Group C Compounds

| Example | mp | % C | % H | % N | % X |
|---|---|---|---|---|---|
| 79 | 178-80 | — | — | — | — |
| 80 | 265-7 | — | — | — | — |
| 80a | — | — | — | — | — |
| 81 | 177-8 | — | — | — | — |
| 81a | — | — | — | — | — |
| 82 | 148-50 | 70.83 | 6.32 | 5.16 | — |
|  |  | 70.71 | 6.40 | 5.23 | — |
| 83 | 227-8 | 69.12 | 5.34 | 5.76 | — |
|  |  | 68.80 | 5.51 | 6.07 | — |
| 83a | — | — | — | — | — |
| 84 | 167-70 | 70.02 | 5.88 | 5.45 | — |
|  |  | 70.04 | 6.04 | 5.57 | — |
| 84a | — | — | — | — | — |
| 85 | 163-5 | 70.83 | 6.31 | 5.16 | — |
|  |  | 70.78 | 6.49 | 5.82 | — |
| 85a | — | — | — | — | — |
| 86 | 272-3 | 69.12 | 5.39 | 5.76 | — |
|  |  | 69.00 | 5.41 | 5.95 | — |
| 86a | — | — | — | — | — |
| 87 | 200—1 | 62.85 | 5.28 | 4.58 | 11.60 |
|  |  | 63.14 | 5.33 | 4.79 | 11.58 |
| 88 | 239-40 | 60.55 | 4.36 | 5.04 | 12.77 |
|  |  | 60.33 | 4.27 | 5.28 | 12.82 |
| 88a | — | — | — | — | — |
| 89 | 240-3 | 61.75 | 4.84 | 4.80 | 12.16 |
|  |  | 62.13 | 4.90 | 4.96 | 12.26 |
| 89a | — | — | — | — | — |
| 90 | 266-8 | 52.19 | 3.75 | 4.35 | 24.81 |
|  |  | 52.32 | 3.69 | 4.39 | 34.75 |
| 90a | — | — | — | — | — |
| 91 | 237-9 | 54.37 | 4.61 | 4.00 | 22.82 |
|  |  | 55.22 | 4.68 | 4.21 | 22.21 |
| 91a | — | — | — | — | — |
| 92 | 148-50 | 58.17 | 5.65 | 3.57 | 20.37 |
|  |  | 57.86 | 5.51 | 4.51 | 20.23 |
| 92a | — | — | — | — | — |
| 93 | 228-30 | 53.59 | 4.20 | 4.17 | 23.77 |
|  |  | 53.65 | 4.19 | 4.64 | 23.34 |
| 93a | — | — | — | — | — |
| 94 | 208-9 | 67.16 | 4.15 | 4.12 | 10.44 |
|  |  | 67.48 | 4.16 | 4.37 | 10.65 |
| 94a | — | — | — | — | — |
| 95 | 179-81 | 71.78 | 5.16 | 3.99 | 5.41 |
|  |  | 71.38 | 5.26 | 4.07 | 5.25 |
| 96 | 197-8 | 70.58 | 4.36 | 4.33 | 5.88 |
|  |  | 70.32 | 4.25 | 4.56 | 5.80 |
| 96a | — | — | — | — | — |

The following examples are presented to illustrate the methods for preparation of the Group C compounds of the present invention.

EXPERIMENTAL PROCEDURES

Example 79

The following procedure is a modified version of one reported by Kametani, et al., *J. Het. Chem.*, 1977, 14, 477.

25 g. of diethyl aminomethylenemalonate, 18 g. of phenylacetone dimethylketal, 300 ml. of dry diphenyl ether and 1.0 g. of TSA.H₂O were mixed and heated under a nitrogen atmosphere at 135°–145° C. for three hours. The mixture was then brought to reflux. After 30 minutes the solution was cooled and extracted with 200 ml. of 2½% aqueous NaOH solution. The basic extracts were acidified yielding a precipitate of ethyl 6-methyl-5-phenyl-4-oxonicotinate. Recrystallization of this material from methylene chloride/ether provided 12.3 g. of white solid, m.p.=178°–180° C.

Example 80

4.0 g. of 6-methyl-5-phenyl-4-oxonicotinate was suspended in 40 g. of 5% aqueous NaOH solution. This suspension was heated at 85°–90° C. for three hours, cooled, acidified. The resulting precipitate of 6-methyl-5-phenyl-4-oxonicotinic acid was dried and recrystallized from acetonitrile. Yield=2.3 g.; m.p.=265°–267° C.

Example 80A 2.31 g. of 6-methyl-5-phenyl-4-oconicotinic acid was mixed with 0.44 g. of NaOH and 50 ml. of methanol. Evaporation of the solvent provided 2.4 g. of sodium 6-methyl-5-phenyl-4-oxonicotinate as a glassy solid.

Example 81

Part A

Ethyl 1-ethyl-6-methyl-5-phenyl-4-oxonicotinate was prepared according to the procedure described by Kametani, et al., *J. Het. Chem.*, 1977, 14, 477.

Part B

Crude ethyl 1-ethyl-6-methyl-5-phenyl-4-oxonicotinate was suspended in 80 g. of 5% aqueous NaOH solution and heated on a steambath for one hour. Acidification of the aqueous mixture gave 1-ethyl-6-methyl-5-phenyl-4-oxonicotinatic acid as a white precipitate (3.3 g.). Recrystallization from acetonitrile provided material melting at 177°–178° C.

Example 81A 3.13 g. of 1-ethyl-6-methyl-5-phenyl-4-oxonicotinic acid, 0.54 g. of NaOH and 50 ml. of methanol were mixed. Evaporation of the solvent provided 3.7 g. of glassy sodium 1-ethyl-6-methyl-5-phenyl-4-oxonicotinic acid.

Example 82

Part A 16.5 g. of ethyl β-methylaminocrotonate, 9.3 ml. of pyridine and 300 ml. of methylene chloride were mixed in a flask fitted with a magnetic stirring bar, a sidearm addition funnel and a CaCl₂ drying tube. 18.3 g. of phenylacetyl chloride was slowly added. Two hours later the reaction mixture was poured into water. The organic layer was separated and evaporated yielding 30 g. of crude ethyl 3-oxo-4-phenyl-2-(methylaminoethylidene)butrate as a yellow oil.

Part B 13.1 g. of crude ethyl 3-oxo-4-phenyl-2-(methylamino-ethylidene)butrate, 5.95 g. of dimethylformamide dimethyl acetal and 25 ml. of dry dimethylformamide were heated to 80° C. under a nitrogen atmosphere for 19 hours. 2.0 ml. of triethylamine and an additional 5.95 g. of dimethylformamide dimethyl acetal were added and the reaction was heated at 80° C. for another 6 hours. The reaction was cooled, poured into water and extracted with methylene chloride. The organic extracts were thoroughly washed with water and dilute CHI and evaporated. The residue of ethyl 1,2-dimethyl-5-phenyl-4-oxonicotinate was tritrated with ether and recrystallized from methylene chloride/ether. Yield=3.2 g.; m.p.=148°-150° C.

Example 83

5.8 g. of ethyl 1,2-dimethyl-5-phenyl-4-oxonicotinate was suspended in 60 ml. of 5% aqueous NaOH solution and heated on a steambath for 2½ hours. The mixture was cooled and acidified. The resulting solid was recrystallized from acetonitrile to yield 1,2-dimethyl-5-phenyl-4-oxonicotinic acid as tan needles. m.p.=227°-228° C.

Example 83A 1.69 g. of 1,2-dimethyl-5-phenyl-4-oxonicitonic acid was mixed with 0.31 g. of NaOH and 50 ml. of methanol. Evaporation of the solid provided 1.9 g. of sodium 1,2-dimethyl-5-phenyl-4-oxonicotinic acid as a glassy solid.

Example 85

Part A 42.4 g. of ethyl β-ethylaminocrotonate, 23.7 g. of pyridine and 700 ml. of methylene chloride were mixed. 46.4 g. of phenylacetyl chloride was added slowly with stirring. Three hours later the mixture was poured into water and the organic layer was separated and evaporated yielding 99 g. of ethyl 3-oxo-4-phenyl-2-(ethylaminoethylidene)butrate as a yellow oil.

Part B 13.8 g. of 3-oxo-4-phenyl-2-(ethylaminoethylidene) butrate, 13.3 g. of dimethylacetamide dimethyl acetal, 25 g. of dry dimethylformamide and 2 ml. of triethylamine were heated at 75°-80° C. under nitrogen for 24 hours. The reaction mixture was cooled and poured into 600 ml. of water. The aqueous suspension was acidified with HCl and extracted with methylene chloride. Evaporation of the solvent provide 10.5 g. of crude ethyl 1-ethyl-2,6-dimethyl-5-phenyl-4-oxonicotinate as a brown oil.

Part C 10.5 g. of crude ethyl 1-ethyl-2,6-dimethyl-5-phenyl-4-oxonicotinate was suspended in 100 g. of 5% aqueous NaOH solution and heated on a steambath for 2 hours. The reaction mixture was cooled and acidified. Extraction with methylene chloride and subsequent evaporation of the solvent yielded 3 g. of 1-ethyl-2,6-dimethyl-5-phenyl-4-oxonicotinate. Recrystallization from acetonitriel provided material with a melting point of 163°-165° C.

Example 85A 1.5 g. of 1-ethyl-2,6-dimethyl-5-phenyl-4-oxonicotinate, 0.24 g. of NaOH and 40 ml. of methanol were mixed. Evaporation of the solvent provided 1.4 g. of sodium 1-ethyl-2,6-dimethyl-5-phenyl-4-oxonicotinate as a glass, solid.

Example 86

Part A 2.68 g. of diethyl aminoethylidene malonate, 18 g. of phenylacetone dimethyl ketal, 1 g. of toluenesulfonic acid monohydrate and 300 ml. of diphenyl ether were heated at 180° C. for 2 hours. Methanol and ethanol began to distill out of the reaction flask and was collected in a Dean-Stark trap. The reaction mixture was then allowed to heat up to 205° C. for an addition 3 hours. A solid formed upon cooling. This was collected by filtration, yielding 4.6 g. of ethyl 2,6-dimethyl-5-phenyl-4-oxonicotinate.

Part B 4.0 g. of ethyl 2,6-dimethyl-5-phenyl-4-oxonicotinate was suspended in 40 g. of 5% aqueous NaOH solution and heated on a steambath for 2 hours. The mixture was cooled and acidified, yielding 3.2 g. of 2,6-dimethyl-5-phenyl-4-oxonicotinic acid. Recrystallization from methanol provided material with a melting point of 272°-273° C. (decomposition).

Example 86A 1.53 g. of 2,6-dimethyl-5-phenyl-4-oxonicotinic acid, 0.23 g. of NaOH and 50 ml. of methanol were mixed. Evaporation of the solvent provided 1.53 g. of sodium 2,6-dimethyl-5-phenyl-4-oxonicotinate as a glassy sold.

Example 87

Part A 42.9 g. of ethyl β-methylaminocrotonate, 25 g. of pyridine and 600 ml. of dry methylene chloride were mixed. 56.7 g. of 4-chlorophenylacetyl chloride was added with stirring. Three hours later the reaction mixture was poured into 300 ml. of water. The methylene chloride layer was separated and evaporated yielding 91 g. of crude ethyl 3-oxo-4-(4'-chlorophenyl)-2-(methylaminoethylidene)butrate as a light yellow oil.

Part B 59.16 g. of ethyl 3-oxo-4-(4'-chlorophenyl)-2-(methylaminoethylidene)burtrate was heated at 80°-85° C. with 48 g. of dimethylformamide dimethyl acetal, 100 ml. of dry dimethylformamide and 8 ml. of triethylamine. After 19 hours, the mixture was cooled, poured into 1000 ml. of water, acidified with dilute HCl and extracted with methylene chloride. Evaporation of the solvent provided ethyl 1,2-dimethyl-5-(4'-chlorophenyl)-4-oxonicotinate as a white solid. m.p=200°-201° C. (acetonitrile).

Example 88

Approximately 30 g. of ethyl 1,2-dimethyl-5-(4'-chlorophenyl)-4-oxonicotinate was suspended in 300 g. of 5% aqueous NaOH solution. 300 ml. of methanol was added and the mixture was refluxed for 7 hours. The resulting solution was cooled and acidified to yield 18.9 g. of 1,2-dimethyl-5-(4'-chlorophenyl)-4-oxonicotinic acid as a white solid, m.p.=239°-240° C. (acetonitrile).

Example 88A 18.5 g. of 1,2-dimethyl-5-(4'-chlorophenyl)-4-oxonicotinic acid was mixed with 2.93 g. of NaOH and 200 ml. of methanol. Evaporation of the solvent provided 19.0 g. of sodium 1,2-dimethyl-5-(4'-chlorophenyl)-4-oxonicotinate as a glassy solid.

Example 89

Part A 14.8 g. of ethyl 3-oxo-4(4'-chlorophenyl)-2-(methylamino-ethylidene)butrate, 10 g. of dimethylacetamide dimethyl acetal, 25 ml. of dry dimethylformamide and 2 ml. of triethylamine were heated at 85° C. for 22½ hours. The reaction was cooled, poured into 400 ml. of water and extracted with methylene chloride. Evaporation of the solvent provided an oily residue of ethyl 1,2,6-trimethyl-5-(4'-chlorophenyl)-4-oxonicotinate.

Part B 13.0 g. of crude ethyl 1,2,6-trimethyl-5-(4'-chlorophenyl)-4-oxonicotinate was suspended in 130 ml. of 5% NaOH in 1:1 methanol/water and refluxed for 6 hours. The reaction mixture was cooled and acidified. Extraction of this material with methylene chloride provided 1.8 g. of 1,2,6-trimethyl-5-(4'-chlorophenyl)-4-oxonicotinic acid. m.p. (acetonitrile) 240°-243° C.

Example 89A 1.8 g. of 1,2,6-trimethyl-5-(4'-chlorophenyl)-4-oxonicotinate, 0.27 g. of NaOH and 50 ml. of methanol were mixed. Evaporation of the solvent provided 1.9 g. of sodium 1,2,6-trimethyl-5-(4'-chlorophenyl)-4-oxonicotinate as a glassy solid.

Example 90

Part A 24.6 g. of ethyl β-methylaminocrotonate was mixed with 250 ml. of methylene chloride and 16 ml. of pyridine. 40 g. of 4-bromophenylacetyl chloride was added with stirring. 2½ hours later, the reaction mixture was poured into water. Separation of the organic layer provided 60.6 g. of ethyl 3-oxo-4-(4'-bromophenyl)-2-(methylamino-ethylidene)butrate after evaporation.

Part B 17 g. of ethyl 3-oxo-4-(4'-bromophenyl)-2-(methylamino-ethylidene)butrate, 12 g. of dimethylformamide dimethyl acetal, 25 ml. of dry dimethyl formamide and 2 ml. of triethylamine were heated under dry nitrogen at 85° C. for 19 hours. The reaction mixture was cooled, poured into 500 ml. of H₂O, acidified with dilute HCl and extracted with methylene chloride. Evaporation of the solid provided 14.3 g. of crude ethyl 1,2-dimethyl-5-(4'-bromophenyl)-4-oxonicotinate.

Part C 14.3 g. of ethyl 1,2-dimethyl-5-(4'-bromophenyl)-4-oxonicotinate was suspended in 140 g. of 5% NaOH in 1:1 methanol/water and refluxed for 4½ hours. The reaction was cooled, diluted with water and acidified. The resulting solid was recrystallized from acetonitrile to yield 6.2 g. of 1,2-dimethyl-5-(4'-bromophenyl)-4-oxonicotinic acid as a white solid, m.p.-266°-268° C. (decomposition).

Example 90A 6.15 g. of 1,2-dimethyl-5-(4'-bromophenyl)-4-oxonicotinic acid was mixed with 0.84 g. of NaOH and 100 ml. of dry methanol. Evaporation of the solvent provided 6.7 g. of sodium 1,2-dimethyl-5-(4'-bromophenyl)-4-oxonicotinate as a tan glassy solid.

Example 91

Part A 15.7 g. of ethyl 3-methylamino-hex-2-enoate, 175 ml. of dry methylene chloride and 10 ml. of pyridine were mixed. 23 g. of 4-bromophenylacetyl chloride was added with stirring. Two hours later the reaction mixture was poured into water and the organic layer was separated and evaporated yielding 45 g. of ethyl 3-oxo-4-(4'-bromophenyl)-2-(methylaminopropylmethylene)-butrate as a brownish oil.

Part B 18.4 g. of 3-oxo-4-(4'-bromophenyl)-2-(methylaminopropylmethylene)butrate was mixed with 12 g. of dimethylformamide dimethyl acetal, 25 ml. of dry dimethyl formamide, and 2 ml. of dry pyridine. The reaction was heated at 85° C. for 21 hours, then cooled, poured into water, acidified and extracted with methylene chloride. Evaporation of the solvent provided 16.5 g. of crude ethyl 1-methyl-2-propyl-5-(4'-bromophenyl)-4-oxonicotinate.

Part C 16.5 g. of ethyl 1-methyl-2-propyl-5-(4'-bromophenyl)-4-oxonicotinate was suspended in 160 g. of 5% NaOH in 1:1 methanol/water. The mixture was refluxed for 10 hours, cooled and acidified. Filtration of the resulting solid provided 9.0 g. of 1-methyl-2-propyl-5-(4'-bromophenyl)-4-oxonicotinic acid. m.p. (acetonitrile)-237°-239° C. (decomposition).

Example 91A 8.8 g. of 1-methyl-2-propyl-5-(4'-bromophenyl)-4-oxonicotinic acid was mixed with 1.1 g. of NaOH and 100 ml. of methanol. Evaporation of the solid provided 8.8 g. of sodium 1-methyl-2-propyl-5-(4'-bromophenyl)-4-oxonicotinate as a glassy powder.

Example 93

Part A 17.0 g. of ethyl 3-oxo-4-(4'-bromophenyl)-2-(methylamino-ethylidene)butrate was mixed with 10 g. of dimethylacetamide dimethyl acetal, 25 g. of dry dimethylformamide and 2 ml. of triethylamine. The reaction mixture was heated at 85° C. for 24½ hours under a nitrogen atmosphere, cooled, poured into water, acidified and extracted with methylene chloride. Evaporation of the solvent and trituration of the residue with ether provided 2.7 g. of crude ethyl 1,2,6-trimethyl-5-(4'-bromophenyl)-4-oxonicotinate as a brownish solid.

Part B 2.7 g. of crude ethyl 1,2,6-trimethyl-5-(4'-bromophenyl)-4-oxonicotinate was suspended in 27 g. of 5% NaOH in 1:1 methanol/water. The reaction mixture was refluxed for 2½ hours, cooled and acidified. Filtration of the resulting solid provided 2.2 g of 1,2,6-trimethyl-5-(4-bromophenyl)-4-oxonicotinic acid. m.p. =228°-230° C. (decomposition).

Example 93A 1.96 g. of 1,2,6-trimethyl-5-(4'-bromophenyl)-4-oxonicotinic acid, 0.26 g. of NaOH and 30 ml. of methanol were mixed. Evaporation of the solvent provided 2.0 g. of sodium 1,2,6-trimethyl-5-(4'-bromophenyl)-4-oxonicotinic acid as a tan glassy solid.

Example 94

Part A 18.4 g. of ethyl β-anilinocrotonate was mixed with 800 ml. of methylene chloride and 8 ml. of pyridine. 17.0 g. of 4-chlorophenyl acetyl chloride was added with stirring. After 2½ hours the reaction mixture was poured into 400 ml. of water and shaken. The methylene chloride layer was separated and evaporated yielding 32 g. of crude ethyl 3-oxo-4-(4'-chlorophenyl)-2-(anilinoethylidene)butrate as a light brown oil.

Part B 32 g. of ethyl 3-oxo-4-(4'-chlorophenyl)-2-(anilinoethylidene)butrate, 15.9 g. of dimethylformamide dimethyl acetal, 40 ml. of dry dimethylformamide and 3.5 ml. of triethylamine were mixed and heated under nitrogen at 80°–85° C. for 18 hours. The reaction was cooled, poured into 600 ml. of water, acidified and extracted with methylene chloride. Evaporation of the solvent provided 35 g. of crude ethyl 2-methyl-1-phenyl-5-(4'-chlorophenyl)-4-oxonicotinate as a brown oil.

Part C 35 g. of crude ethyl 2-methyl-1-phenyl-5-(4'-chlorophenyl)-4-oxonicotinate was suspended in 350 g. of 5% NaOH in 1:1 methanol/water and refluxed for 6 hours. The reaction mixture was cooled. This yielded a precipitate of sodium 2-methyl-1-phenyl-5-(4'-chlorophenyl)-4-oxonicotinate which was collected by filtration and resuspended in dilute aqueous HCl to provide 5.3 g. of 2-methyl-1-phenyl-5-(4'-chlorophenyl)-4-oxonicotinic acid, m.p. (acetonitrile)=209°–209° C.

Example 94A 5.25 g. of 2-methyl-1-phenyl-5-(4'-chlorophenyl)-4-oxonicotinic acid, 0.68 g. of NaOH and 100 g. of dry methanol were mixed. Evaporation of the solvent provided 5.0 g. of sodium 2-methyl-1-phenyl-5-(4'-chlorophenyl)-4-oxonicotinate as a glassy solid.

D. N-alkyl-2,6-diaryl-4-oxonicotinates

In still another preferred aspect, this invention relates to compounds of the formula:

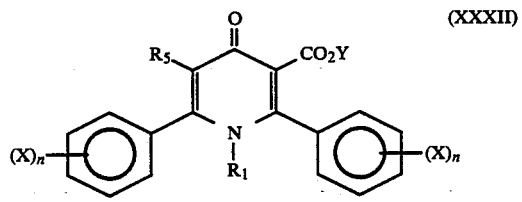
(XXXII)

wherein $R_1$ is a ($C_1$–$C_6$) alkyl group; $R_5$ is a hydrogen atom, a ($C_1$–$C_4$) alkyl group or a halogen atom; Y is a hydrogen atom or a ($C_1$–$C_6$) alkyl group; X is a hydrogen atom, a halogen atom, a trihalomethyl group, a ($C_1$–$C_6$) alkyl group, a nitro group, a cyano group or a ($C_1$–$C_6$) alkoxy group; n is the integer 1 or 2; and the agronomically acceptable salts thereof.

Among the preferred compounds of the present invention are compounds of Group D, formula (XXXII) wherein $R_1$ is a ($C_1$–$C_6$) alkyl, ($C_1$–$C_4$) haloalkyl, alkoxy ($C_1$–$C_4$) alkyl ($C_1$–$C_4$), aryl ($C_6$–$C_{10}$) alkyl ($C_1$–$C_4$), or ($C_3$–$C_6$) alkenyl; Y is hydrogen, ($C_1$–$C_6$) alkyl, an alkali or alkaline earth metal cation, or an ammonium or mono-, di-, tri-, or quaternary ammonium cation; $R_5$ is hydrogen, ($C_1$–$C_6$) alkyl, or halogen; X is hydrogen, halogen, trihalomethyl, ($C_1$–$C_6$) alkyl, ($C_1$–$C_6$) alkoxy, nitro or cyano; and n is an integer from 1 to 2.

Among the more preferred compounds of the present invention are compounds of Group D, Formula (XXXII) wherein $R_1$ is ($C_1$–$C_3$) alkyl; $R_5$ is hydrogen or bromine; Y is hydrogen, sodium or potassium; X is hydrogen or halogen; is an integer 1 or 2.

Among the most preferred compounds of this invention are compounds of Group D Formula (XXXII) wherein $R_1$ is methyl or ethyl; $R_5$ is a hydrogen atom; and Y is hydrogen or a sodium or potassium cation; X is hydrogen, chlorine or fluorine; and n is 1; and the agronomically acceptable acid addition salts thereof.

Typical compounds encompassed by the present invention include:
1-methyl-2,6-diphenyl-4-oxonicotinic acid;
1-propyl-2,6-diphenyl-4-oxonicotinic acid;
1-hexyl-2,6-diphenyl-4-oxonicotinic acid;
5-bromo-1-methyl-2,6-diphenyl-4-oxonicotinic acid;
5-chloro-1-ethyl-2,6-diphenyl-4-oxonicotinic acid;
1,5-dimethyl-2,6-diphenyl-4-oxonicotinic acid;
1-methyl-2,6-di(4'-chlorophenyl)-4-oxonicotinic acid;
1-butyl-2,6-di(4'-chlorophenyl)-4-oxonicotinic acid;
1-ethyl-2,6-di(3'-chlorophenyl)-4-oxonicotinic acid;
1-methyl-2,6-di(2'-chlorophenyl)-4-oxonicotinic acid;
1-methyl-2,6-di(4'-fluorophenyl)-4-oxonicotinic acid;
1-methyl-2,6-di(3'-fluorophenyl)-4-oxonicotinic acid;
5-bromo-1-methyl-2,6-di(4'-fluorophenyl-4-oxonicotinic acid;
1-ethyl-2,6-di(3',4'-dichlorophenyl)-4-oxonicotinic acid;
1-propyl-2,6-di(2',4'-dichlorophenyl)-4-oxonicotinic acid;
1-methyl-2,6-di(4'-trifluorophenyl)-4-oxonicotinic acid;
1-methyl-2-(4'-fluorophenyl)-6-phenyl-4-oxonicotinic acid;
1-methyl-2-(4'-chlorophenyl)-6-(4'-fluorophenyl)-4-oxonicotinic acid;
1-chloro-2-(4'-chlorophenyl)-6-phenyl-4-oxonicotinic acid;
1-pentyl-6-(4'-fluorophenyl)-2-phenyl-4-oxonicotinic acid;
and the agronomically acceptable salts thereof.

The compounds of the present invention can be prepared by various synthetic routes found in the art. In particular, the compounds of the present invention can be prepared by the following reaction sequence:

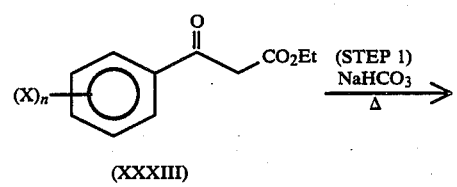

(XXXIII)

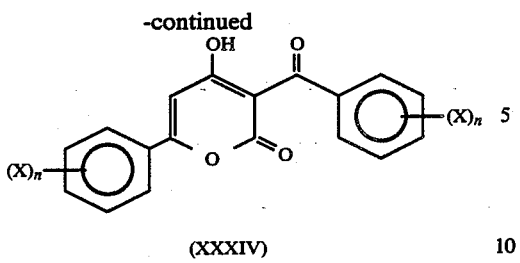

(XXXIV)

II
(XXXIV) STEP 2 →

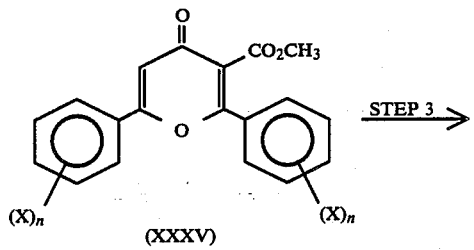

(XXXV)

STEP 3 →

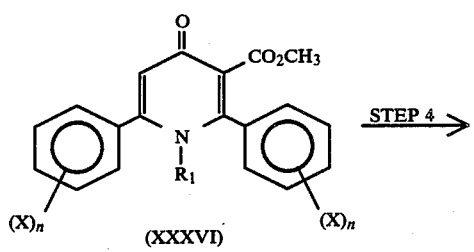

(XXXVI)

STEP 4 →

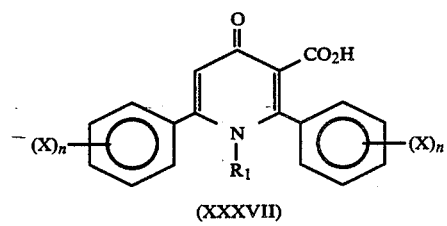

(XXXVII)

Step No. 1
(a) NaHCO$_3$, Na$_2$CO$_3$;
(b) chlorobenzene, dichlorobenzene, toluene, decalin, other inert solvents;
(c) temp.: 50–250° C., preferably 100–200° C. and
(d) similar to procedure described F. Arndt, B. Eistert, H. Schole and F. Aron, Ber., 69, 2373 (1936).

Step No. 2
(a) methanol;
(b) trimethyl orthoformate dessicant;
(c) H$_2$SO$_4$, HCl, other strong acids;
(d) temp.: 25–200° C., preferably 50–150° C.

Step No. 3
(a) alkyl amine;
(b) inert solvent, alcohols, ethers, hydrocarbons, water;
(c) acid catalyst optional;
(d) temp.: 0–150° C., preferably 25–50° C.

Step No. 4
(a) aqueous base;
(b) optional inert co-solvent, methanol, DMSO;
(c) temp.: 20–150° C., preferably 50–100° C.
(d) any acid to neutralize.

Another route to the compounds of Group D, formula (XXXII) is:

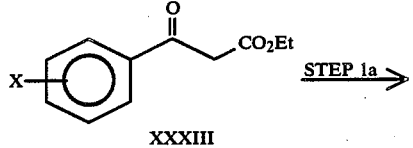

XXXIII

STEP 1a →

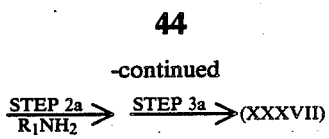

Step No. 1a
(a) 1:10 P$_2$O$_5$/CH$_3$SO$_3$H by weight;
(b) temp.: 20–150° C., preferably 20–60° C.
Other steps: same as above Still another route to the compounds of Group D, formula (XXXII) of the present invention is shown by the following reaction sequence:

(XXXIII) $\xrightarrow[R_1NH_2]{\text{STEP 1b}}$

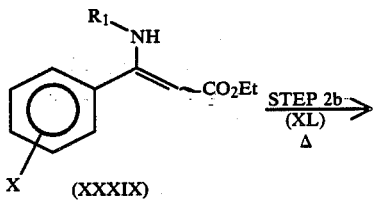

(XXXIX)

$\xrightarrow[\Delta]{\text{STEP 2b}}$ (XL)

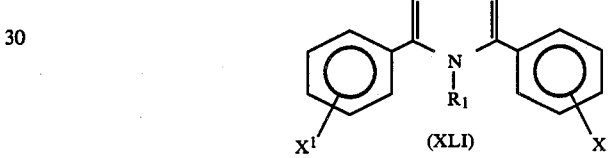

(XLI)

Step No. 1b:
(a) RNH$_2$
(b) inert solvent, methanol, H$_2$O
(c) acid catalyst optional
(d) temp.: 20–150° C., preferably 20–100° C.

Step No. 2b:
(a) run in inert solvent (methylene chloride, benzene, toluene, ether)
(b) acid acceptor optional (pyridine, Et$_3$N)
(c) temp.: 0°–150° C., preferably 10–50° C.
(d) residue heated 100–200° C., preferably 150–180° C.

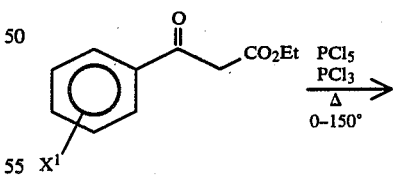

$\xrightarrow[\Delta\ 0-150°]{\text{PCl}_5\ \text{PCl}_3}$

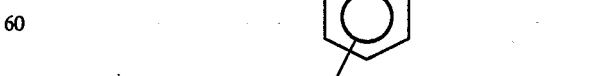

(XL)

Yet another route to the compounds of Group D, formula (XXXII) of the present invention is shown by the following reaction equation:

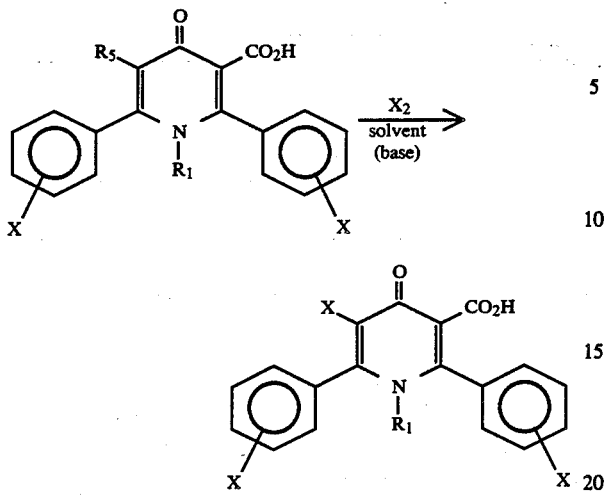

(a) carried out in compatable solvent (MeOH, water)
(b) room temperature
(c) optional addition of base (NaOH), NA₂CO₃, etc.).

Tables VIII and IX below are presented to illustrate the more preferred compounds of this aspect of the present invention and related compounds and the analytical data for these compounds.

TABLE VIII

List of Group D Compounds

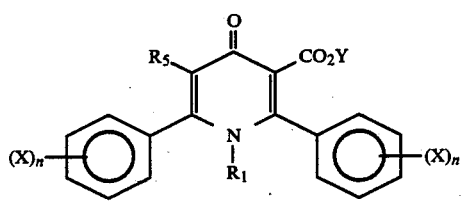
(XXXII)

| Example No. | R₁ | R₅ | X | X' | Y |
|---|---|---|---|---|---|
| 97 | H | H | H | H | H |
| 97a | H | H | H | H | Na |
| 98 | Me | H | H | H | Et |
| 99 | Me | H | H | H | Me |
| 100 | Me | H | H | H | H |
| 100a | Me | H | H | H | Na |
| 101 | Et | H | H | H | H |
| 101a | Et | H | H | H | Na |
| 102 | Me | H | 4-Br | 4-Br | H |
| 102a | Me | H | 4-Br | 4-Br | Na |
| 103 | Me | H | 4-Br | 4-Br | Et |
| 104 | Me | H | 4-F | 4-F | H |
| 104a | Me | H | 4-F | 4-F | Na |
| 105 | Me | H | 4-Cl | 4-Cl | H |
| 105a | Me | H | 4-Cl | 4-Cl | Na |
| 106 | Me | H | 4-CH₃ | 4-CH₃ | H |
| 106a | Me | H | 4-CH₃ | 4-CH₃ | Na |
| 107 | Me | H | H | 4-CH₃ | H |
| 107a | Me | H | H | 4-CH₃ | Na |
| 108 | Me | Br | H | H | H |
| 108a | Me | Br | H | H | Na |
| 109 | Pr | H | H | H | H |
| 109a | Pr | H | H | H | Na |

TABLE IX

| Example No. | mp °C. | % C | % H | % N |
|---|---|---|---|---|
| 97 | 228–30 | 74.21 | 4.50 | 4.80 |
|  |  | 74.46 | 4.40 | 5.15 |
| 97a | — | — | — | — |
| 98 | 177–9 | 75–65 | 5.74 | 4.20 |
|  |  | 75.49 | 5.83 | 4.45 |
| 99 | 255–7 | 75.22 | 5.37 | 4.39 |
|  |  | 75.13 | 5.51 | 4.46 |
| 100 | 209–11 | 74.74 | 4.95 | 4.59 |
|  |  | 74.04 | 5.04 | 4.47 |
| 100a | — | — | — | — |
| 101 | 210–13 | 75.22 | 5.37 | 4.39 |
|  |  | 75.28 | 5.37 | 4.22 |
| 101a | — | — | — | — |
| 102 | 197 | 49.27 | 2.83 | 3.03 |
|  |  | 49.27 | 2.86 | 3.34 |
| 102a | — | — | — | — |
| 103 | 218–20 | 51.35 | 3.49 | 2.85 |
|  |  | 50.45 | 3.43 | 3.03 |
| 104 | 191–3 | 66.86 | 3.84 | 4.10 |
|  |  | 58.41 | 3.67 | 4.25 |
| 104a | — | — | — | — |
| 105 | 187–90 | 60.98 | 3.50 | 3.74 |
|  |  | 60.75 | 3.53 | 4.29 |
| 105a | — | — | — | — |
| 106 | 209–12 | 75.65 | 5.74 | 4.20 |
|  |  | 74.89 | 5.79 | 4.26 |
| 106a | — | — | — | — |
| 107 | 158–63 | 75.22 | 5.37 | 4.39 |
|  |  | 72.13 | 5.50 | 4.02 |
| 107a | — | — | — | — |
| 108 | 242–3 | 59.39 | 3.67 | 3.65 |
|  |  | 60.44 | 3.77 | 4.15 |
| 108a | — | — | — | — |
| 109 | 166.7 | 75.20 | 6.31 | 4.18 |
|  |  | 75.14 | 5.85 | 4.28 |
| 109a | — | — | — | — |

EXPERIMENTAL PROCEDURES

Example 98

Part a

A 500 ml single neck flask was fitted with a magnetic stirrer and an N₂ inlet. 20 gms of ethyl benzoylacetate (0.104 moles) was dissolved in 200 gms of 1:10 P₂O₅/methanesulfonic acid and added to the flask. The homogeneous reaction mixture was heated to 40° and maintained at that temperature for four days. The mixture was then cooled and diluted with 100 mls of methylene chloride. This solution was added in 50 ml portions to 1000 mls of cold water in a separatory funnel. The separatory funnel was shaken vigorously after each addition. The organic layer was then washed with water and evaporated leaving an oily residue that crystallized from ether. The isolated yield of 2,6-diphenyl-3-ethoxycarbonyl-4-pyrone was 10.5 gms (63%). mp=102°–3°.

Part b 3.5 gms of 2,6-diphenyl-3-ethoxycarbonyl-4-pyrone was dissolved in 33 mls of methanol. 2 mls of glacial acetic acid was added. 13.3 mls of 40% aqueous methylamine was then added very slowly at room temperature. After 6 hours the reaction mixture was diluted with 200 mls of water and extracted with methylene chloride. Evaporation yielded 3.5 gms of ethyl 2,6-diphenyl-1-methyl-4-oxonicotinate which was recrystallized from methylene chloride/ether. mp=177°–9°.

Example 99

Part a

A 200 ml flask was fitted with a N₂ inlet, a magnetic stirring bar and a condenser. 50 mls of methanol, 8.0 gms of trimethyl orthoformate, 5.2 gms of concentrated H₂SO₄ and 5.0 gms of 3-benzoyl-4-hydroxy-6-phenylpyr-2-one were added. The resulting mixture was then refluxed for 3 days, cooled, poured into water and extracted with methylene chloride (300 mls). The organic extracts were combined and washed with water. Removal of the solvent provided 4.4 gms of 2,6-diphenyl-3-methoxycarbonyl-pyr-4-one (85%). Recrystallization from methylene chloride/ether provide material with a melting point=150°-1°.

Part b 3.0 gms of 2,6-diphenyl-3-methoxycarbonyl-pyr-4-one, 33 mls of methanol, 13.3 mls of 40% aqueous methylamine and 2 mls of glacial acetic acid were mixed at room temperature. The next day the mixture was diluted with water. Filtration of the resulting suspension yielded 2.5 gms of methyl 2,6-diphenyl-1-methyl-4-oxonicotinate. Recrystallization from methanol provided material at 255°-7°.

Example 100

2.5 gms of methyl 2,6-diphenyl-1-methyl-4-oxonicotinate was suspended in 28 mls of 5% aqueous sodium hydroxide 8 hours, cooled, and filtered to remove residual insolubles. The clear basic solution was then acidified with diluted HCl to provide a white precipitate of 2,6-diphenyl-1-methyl-4-oxonicotinic acid. Recrystallization from methylene chloride/ether provided 2.4 gms of product. mp=209°-11°(dec).

Example 100a 1.73 gms of 2,6-diphenyl-1-methyl-4-oxonicotinic acid was suspended in 50 mls of dry methanol. 0.25 gms of NaOH was added. After the carboxylic acid and the NaOH dissolved the solvent was removed yielding 1.75 gms of sodium 2,6-diphenyl-1-methyl-4-oxonicotinate as a glassy solid.

Example 101

3.5 gms of 2,6-diphenyl-3-ethoxycarbonyl-pyr-4-one, 33 mls of methanol, 5 mls of water and 2 mls of glacial acetic acid were mixed. 7.6 mls of 70% aqueous ethylamine was then added slowly and the resulting mixture was allowed to stand at room temperature for 24 hours. The mixture was then diluted with 100 mls of water. The pH was adjusted to 2. Extraction with methylene chloride and evaporation of the solvent provided 3.0 gms of crude ethyl 1-ethyl-2,6-diphenyl-4-oxonicotinate as a brown oil. This material was dissolved in 20 mls of methanol. This solution was then added to 40 mls of 5% aqueous NaOH and heated on a steambath for 5 hours. The reaction mixture was cooled and acidified. Extraction with methylene chloride (3×50 mls) yielded an oily solid after evaporation. Crystallization from methylene chloride/ether yielded 1.6 gms of 1-ethyl-2,6-diphenyl-4-oxonicotinic acid. mp=210°-3° (dec).

Example 101a 1.38 gms of 1-ethyl-2,6-diphenyl-4-oxonicotinic acid was treated with 0.19 gms of NaOH in 50 mls of dry methanol. Evaporation of the solvent provided 1.40 gms of sodium 1-ethyl-2,6-diphenyl-4-oxonicotinate as a glassy solid.

Example 104

Part a 25 gms of ethyl 4-fluorobenzoylacetate was dissolved in 250 gms of 1:10 P$_2$O$_5$/methanesulfonic acid and heated at 45° for 4 days. The mixture was cooled, poured into 1200 mls of water and extracted with (3×100 mls) methylene chloride. Evaporation of the solvent and chromatography of the resulting oil (silica gel/ether) provided 12.9 gms of crystalline 2,6-di(4'-fluorophenyl)-3-ethoxycarbonyl-pyr-4-one. mp=113°-4°.

Part b 5 gms of 2,6-di(4'-fluorophenyl)-3-ethoxycarbonyl-pyr-4-one, 47 mls of methanol and 2.9 mls of glacial acetic acid were mixed. 19 mls of 40% aqueous methylamine was added slowly. Three hours later the reaction mixture was poured into 200 mls of water and extracted with methylene chloride (2×100 mls). This provided 5.4 gms of crude ethyl 1-methyl-2,6-di(4'-fluorophenyl)-4-oxonicotinate as a brown oil.

The crude ester was suspended in 50 mls of 5% aqueous NaOH solution and heated for 3 hours. The mixture was cooled and acidified. Extraction with methylene chloride provided a yellow solid which was recrystalized from methylene chloride/ether to provide 3.6 gms of 1-methyl-2,6-di(4'-fluorophenyl)-4-oxonicotinic acid. mp=191°-3°.

Example 104a 3.45 gms of 1-methyl-2,6-di(4'-fluorophenyl)-4-oxonicotinic acid was mixed with 0.445 gms of NaOH and 70 mls of methanol. Evaporation of the solvent provided 3.1 gms of sodium 1-methyl-2,6-di(4'-fluorophenyl)-4-oxonicotinate as a glassy solid.

Example 105

Part a 15 gms of ethyl 4-chlorobenzoylacetate was mixed with 150 gms of 1:10 P$_2$O$_5$/methanesulfonic acid and heated at 45° for 4 days. The cooled reaction mixture was poured into a separatory funnel containing 1500 mls of cold water and the resulting mixture was shaken for several minutes. Extraction with methylene chloride and chromatograph, of the resulting crude product (silica gel/ether) provided 5.5 gms of ethyl 2,6-di(4'-chlorophenyl)-3-ethoxycarbonyl-pyr-4-one. mp=130°.

Part b 5.0 gms of ethyl 2,6-di(4'-chlorophenyl)-3-ethoxycarbonyl-pyr-4-one, 100 mls of methanol, 19 mls of 40% aqueous methylamine, 19 mls of water and 2.9 mls of glacial acetic acid were mixed and allowed to stand at room temperature for 3 hours. The mixture was poured into water and extracted with methylene chloride to provide 5 gms of crude ethyl 1-methyl-2,6-di(4-chlorophenyl)-4-oxonicotinate as a yellowish semi-solid.

The ester was then suspended in 50 mls of 5% aqueous NaOH solution. 20 mls of methanol was added to improve solubility. The mixture was heated on a steambath for 3 hours, cooled, and acidifed with dilute HCl to provide a white precipitate. Recrystallization from methylene chloride/ether, yielded 3.4 gms of 1-methyl-2,6-di(4'-chlorophenyl)-4-oxonicotinic acid. mp=187°-90°.

Example 105a 3.32 gms of 1-methyl-2,6-di(4'-chlorophenyl)-4-oxonicotinic acid, 0.39 gms of NaOH and 50 mls of methanol were mixed. Evaporation of the solvent provided 3.4 gms of sodium 1-methyl-2,6-di(4'-chlorophenyl)-4-oxonicotinate as a glass solid.

Example 107

Part a

A one liter flask was fitted with a mechanical stirrer, $CaCl_2$ drying tube, condenser and a sidearm addition funnel. 100 gms of $PCl_5$ was placed in the flask. 39 gms of ethyl 4-methylbenzoylacetate and 100 gms of $PCl_3$ were mixed and slowly added to the $PCl_5$ at room temperature. The reaction mixture evolved HCl. After 30 minutes the mixture was cautiously refluxed for 2 hours. At this time $PCl_3$ and $POCl_3$ were distilled from the reaction mixture at reduced pressure. The residue was then distilled at 0.5 mm (bp=116°-121°) to provide 32 gms of β-chloro-4-methylcinnamoyl chloride as a clear oil.

Part b 10.0 gms of ethyl B-methylaminocinnamate, 9.6 gms of pyridine and 75 mls of dry methylene chloride were mixed in a flask under a dry nitrogen atmosphere. 10 gms of β-chloro-4-methylcinnamoyl chloride in 25 mls of methylene chloride were added at ambient temperatures. After 2 hours the reaction mixture was poured into water and extracted with methylene chloride. Evaporation of the solvent provided 18 gms of a brown oil. This material was heated (160°-178°) for 15 minutes (HCl evolution), cooled, and taken up in dilue aqueous NaOH. Acidification of the basic extracts and recrystallization of the resulting solid from methanol provided 0.8 gms of 1-methyl-2-phenyl-6-(4'-methylphenyl)-4-oxonicotinic acid. mp=158°-63° (dec).

Example 107a 0.64 gms of 1-methyl-2-phenyl-6-(4'-methylphenyl)-4-oxonicotinic acid, 0.09 gms of NaOH and 30 mls of methanol were mixed. Evaporation of the solvent provided 0.6 gms of sodium 1-methyl-2-phenyl-6-(4'-methylphenyl)-4-oxonicotinate as a glassy solid.

Example 108

3.75 gms of 1-methyl-2,6-diphenyl-4-oxonicotinic acid was dissolved in 40 mls of methanol. The pH was adjusted to 12 with the addition of aqueous NaOH. A methanolic solution of bromine (2.95 gms $Br_2$ in 50 mls methanol) was added. Additional NaOH was added as required to maintain a basic medium. Removal of the solvent yielded a semi-solid that was taken up in 100 mls of water. Water insoluble material was removed by filtration. Acidification of the aqueous solution provided 3.0 gms of 5-bromo-1-methyl-2,6-diphenyl-4-oxonicotinic acid (mp 242°-3°, with decomposition) as a white solid.

Example 108a 2.5 gms of 5-bromo-1-methyl-2,6-diphenyl-4-oxonicotinic acid, 0.286 gms of NaOH and 50 mls of dry methanol were mixed. Evaporation of the solvent provided 2.6 gms of sodium 5-bromo-1-methyl-2,6-diphenyl-4-oxonicotinate as a tan glassy solid.

Example 109

4.0 gms of 2,6-diphenyl-3-ethoxycarbonyl-pyr-4-one, 50 mls of glacial acetic acid were mixed. 8.1 gms of n-propylamine and 6 mls of water was added slowly at room temperature. After 3 hours an additional 14 mls of water, 12 mls of 6% HCl and enough methanol to bring everything into solution, was added. The next day this acidic reaction misture was poured into water and extracted with methylene chloride (2×100 mls). Evaporation of the organic extracts yield 4.4 gms of crude nicotinate ester which was suspended in 50 mls of 5% aqueous NaOH and heated at 85° for 4 hours. The resulting solution was acidified with HCl and extracted with methylene chloride (2×50 mls). Evaporation of the solvent yielded a solid mass. Recrystallization from ether provided 1.5 gms of 1-propyl-2,6-diphenyl-4-oxonicotinic acid. mp=166°-7°.

Example 109a 1.5 gms of 1-propyl-2,6-diphenyl-4-oxonicotinic acid, 0.202 gms of NaOH and 50 mls of dry methanol were mixed. Evaporation of the solvent yielded 1.5 gms of sodium 1-propyl-2,6-diphenyl-4-oxonicotinate as a white glassy solid.

The compounds of the invention are particularly useful as chemical hybridization agents in cereal crops, such as wheat, barley, corn, rice, sorghum, millets, oats, rye, triticale and the like. When used as chemical hybridization agents, the compounds effectively induce a high degree of selective male sterility, that is, without also inducing significant female sterility, in the treated plants and without causing significant growth inhibition of the treated plants. As used herein, the term male sterility includes both actual male sterility, as evidenced by a lack of male flower parts or by sterile pollen, and functional male sterility, in which the male flower parts are unable to cause pollination. The compounds of the invention also cause other plant growth regulatory responses, such as for example, control of flowering, control of fruiting and inhibition of seed formation in non-cereal species and other related growth regulatory responses.

When used as plant growth regulators, the compounds of the invention are applied in any amount which will be sufficient to effect the desired plant response without causing any undesirable or phytotoxic response. For example, when the compounds of the invention are used as chemical hybridization agents, they are generally applied to the crops to be treated at a rate of about 1/32 to about 20 pounds per acre and preferably about ¼ to about 10 pounds per acre. The rate of application will vary depending on the crop being treated, the compound being used for treatment, and related factors.

To obtain hybrid seed, the following procedure is generally employed. The two parents to be crossed are planted in alternate strips. The female parent is treated with a compound of the invention. The male-sterile female parent thus produced will be pollinated by pollen from the other, male-fertile, male parent, and the seed produced by the female parent will be hybrid seed which can then be harvested by conventional means.

A preferred method of applying a compound of the invention as a chemical hybridization agent is by foliar application. When this method is employed, selective male sterility is most effectively induced when the compound is applied between anther initiation and meiosis. The compounds of the inventions may also be applied as a seed treatment by soaking the seed in a liquid formulation containing the active compound or by coating the seed with the compound. In seed treatment applications, the compounds of the invention will generally be applied at a rate of about ¼ to about 10 pounds per hundred weight of seed. The compounds of the invention are also effective when applied to the soil or to the water surface in rice crops.

The compounds of the invention can be used as plant growth regulators either individually or in mixtures. For example, they can be used in combination with other plant growth regulators, such as auxins, gibberellins, ethylene-releasing agents such as ethephon, pyridones, pyridazinones, cytokinins, maleic hydrazide, succinic acid 2,2-dimethylhydrazide, chlorine and its salts (2-chloroethyl) trimethylammonium chloride, triiodobenzoic acid, tributyl-2,4-dichlorobenzylphosphonium chloride, polymeric N-vinyl-2-oxazolidinones, tri)dimethylaminoethyl) phosphate and its salts, and N-dimethylamino-1,2,3,6-tetrahydrophthalamic acid and its salts, and the like, and under some conditions may be used advantageously with other agricultural chemicals such as herbicides, fungicides, insecticides, and plant bactericides.

A compound of the invention can be applied to the growth medium or to plants to be treated either by itself or, as is generally done, as a component in a growth regulant composition or formulation which also comprises an agronomically acceptable carrier. By "agronomically acceptable carrier" is meant any substance which can be used to dissolve, disperse, or diffuse a compound in the composition without impairing the effectiveness of the compound and which by itself has no significant detrimental effect on the soil, equipment, crops or agronomic environment. Mixtures of the compounds of the invention may also be used in any of these formulations. The compositions of the invention can be either solid or liquid formulations or solutions. For example, the compounds can be formulated as wettable powders, emulsifiable concentrates, dusts, granular formulations, aerosols, or flowable emulsion concentrates. In such formulations, the compounds are extended with a liquid or solid carrier and, when desired suitable surfactants are incorporated.

It is usually desirable, particularly in foliar applications, to incude adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual".

The compounds of the invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can vary from about 2% to about 98% by weight with a preferred range being from about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent or surfactant which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkyl-benzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates of usually abut 10% to 60% by weight and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, preferably about 40% to 75%. A dispersing agent may generally constitute about 0.5% to about 3% by weight of the composition, and a wetting agent may generally constitute from about 0.1% to about 5% by weight of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing abut 20% to 80% of the active ingredient are commonly made and are subsequently diluted to about 1% to 10% by weight use concentration.

Granular formulations can be prepared by impregnating a solid such as granular Fuller's earth, vermiculite, ground corn cobs, seed hulls, including bran or other grain hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The active compound will usually comprise about 2 to 15% by weight of the granular formulations.

Salts of the compounds of the invention can be formulated and applied as aqueous solutions. The salt will typically comprise about 0.05 to about 50% by weight preferably about 0.1% to about 10%, of the solution.

These compositions can also be further diluted with water if desired prior to actual application. In some applications, the activity of these compositions can be enhanced by incorporating into the composition an adjuvant such as glycerin, methylethylcellulose, hydroxyethylcellulose, polyoxyethylenesorbitan monooleate, polypropylene glycol, polyacrylic acid, polyethylene sodium malate, polyethylene oxide, or the like. The adjuvant will generally comprise about 0.1 to about 5% by weight, preferably about 0.5 to about 2%, of the composition. Such compositions can also optionally include an agronomically-acceptable surfactant.

The compounds of the invention can be applied as sprays by methods commonly employed, such as conventional hydraulic sprays, aerial sprays, and dusts. For low-volume applications, a solution of the compound is usually used. The dilution and volume of application will usually depend upon such factors as the type of equipment employed, the method of application, the area to be treated and the type and stage of development of the crop being treated.

The following is a typical tank mix formulation for the foliar application of sodium 1-ethyl-6-methyl-2-(4-chlorophenyl)-4-oxonicotinate on winter wheat at a rate of 0.25 lbs./A:
0.25 lbs. of oxonicotinate salt
1 pt. of Triton AG 98®
dulute to 50 gals. with water.
This mixture is then foliar spray-applied to the wheat plants at a rate of 50 gals/A.

The following examples will further illustrate the chemical hybridization activity of the compounds of the invention but are not intended to limit the invention in any way.

EXAMPLE 110

Chemical Hybridization Activity

The following procedures are used to evaluate the activity of the compounds of the invention for inducing male sterility in cereals.

An awned variety (Fielder) and an awnless variety (Mayo-64) of spring wheat are planted at the rate of 6 to 8 seeds per 6 inches pot containing a sterile medium of 3 parts soil and 1 part humus. The plants are grown under short-day (9 hour) conditions for the first 4 weeks to obtain good vegatative growth before flower initiation. The plants are then moved to long-day (16 hour) conditions which are provided by high intensity lights in the greenhouse. The plants are fertilized at 2, 4, and 8 weeks after planting with a water soluble fertilizer (16-25-16) at the rate of 1 tsp/gal of water, and are frequently sprayed with isotox for aphid control and dusted with sulfur for powdery mildew control.

Test compounds are foliarly applied to the awned female plants when these plants reach the flag leaf emergence stage (stage 8 on Feekes' scale). All compounds are applied in a carrier volume of 50 gal/A containing a surfactant, such as Triton X-100 at the rate of 20 oz/50 gal.

After spike emergence but before anthesis, 4 to 6 spikes per pot are bagged to prevent outcrossing. At the first signs of flower opening, two spikes per pot are cross pollinated, using the approach method, with the awnless male percent. As soon as the seeds become plainly visible, spike length is measured and seeds per spikelet counted in both bagged and crossed spikes. Male sterility can then be calculated as percent inhibition of seed set in bagged spikes of treated plants, and female fertility in crossed spikes can be calculated as percent of control seed set. After maturity the seed on crossed spikes are planted for determination of percent hybridization.

Percent sterility, percent fertility, and percent height inhibition are calculated from the following formulas:

a. % Sterility = $(S_c - S_t/S_c) \times 100$
   $S_c$ = seeds/spikelet in bagged spikes of control plants.
   $S_t$ = seeds/spikelet in begged spikes of treated plants
b. % Fertility = $(F_t/F_c) \times 100$
   $F_t$ = seeds/spikelet in approach crossed spikes of treated plants
   $F_c$ = seeds/spikelet in unbagged spikes of control plants
c. % Height inhibition = $(H_c - H_t/H_c) \times 100$
   $H_c$ = Height of control plants
   $H_t$ = Height of treated plants Table III summarizes typical results obtained in the evaluation of compounds of the invention. A dash indicates that no determination of value was made.

TABLE X

Biological Data (Wheat Greenhouse Data)
% Male Sterility at Dosage (lbs./A)

| Example # | 8 | 4 | 2 | 1 | ½ | ¼ | ⅛ |
|---|---|---|---|---|---|---|---|
| 1 | \multicolumn{7}{l}{not active at 8 lbs/A or below} | | | | | | |
| 2 | not active at 8 lbs./A or below | | | | | | |
| 3 | not active at 8 lbs/A or below | | | | | | |
| 4a | — | 100 | 100 | 77 | 36 | — | — |
| 5 | — | — | — | — | — | — | — |
| 5a | 100 | — | 100 | — | 43 | — | 2 |
| 6 | — | — | — | — | — | — | — |
| 6a | 100 | — | 85 | — | 18 | — | 54 |
| 7 | — | — | — | — | — | — | — |
| 7a | not active at 8 lbs/A or below | | | | | | |
| 8 | — | — | — | — | — | — | — |
| 8a | — | — | 98 | — | 34 | — | 1 |
| 9 | — | — | — | — | — | — | — |
| 9a | 99 | — | 88 | — | 32 | — | 5 |
| 10 | — | — | — | — | — | — | — |
| 10a | — | — | 100 | — | 100 | — | 13 |
| 11 | — | — | — | — | — | — | — |
| 11a | — | 88 | — | 2 | — | 2 | — |
| 12 | — | — | — | — | — | — | — |
| 12a | not active at 8 lbs/A or below | | | | | | |
| 13 | — | — | — | — | — | — | — |
| 13a | — | 100 | 100 | 92 | 55 | 12 | — |
| 14 | not active at 8 lbs/A or below | | | | | | |
| 15 | not active at 8 lbs/A or below | | | | | | |
| 16 | — | — | — | — | — | — | — |
| 16a | — | 100 | 100 | 100 | 96 | 91 | — |
| 17 | — | 100 | 100 | 100 | 96 | 91 | — |
| 17a | 100 | — | 100 | 18 | 0 | — | 0 |
| 18 | — | — | — | — | — | — | — |
| 18a | — | — | — | 100 | 66 | 100 | 41 |
| 19 | — | — | — | — | — | — | — |
| 19a | not active at 8 lbs/A or below | | | | | | |
| 20 | — | — | — | — | — | — | — |
| 20a | not active at 8 lbs/A or below | | | | | | |
| 21 | — | — | — | — | — | — | — |
| 21a | not active at 8 lbs/A or below | | | | | | |
| 22 | — | — | — | — | — | — | — |
| 22a | 100 | — | — | — | — | — | — |
| 23 | — | — | — | — | — | — | — |
| 23a | not active at 8 lbs/A or below | | | | | | |
| 24 | — | — | — | — | — | — | — |
| 24a | 10 | — | 8 | — | 19 | — | 15 |
| 25 | — | — | — | — | — | — | — |
| 25a | — | 55 | 49 | 0 | 0 | 0 | — |
| 26 | — | — | — | — | — | — | — |
| 26a | — | 94 | 7 | 15 | 0 | 2 | — |
| 27 | — | — | — | — | — | — | — |
| 27a | — | 100 | 100 | 57 | 0 | 2 | — |
| 28 | — | — | — | — | — | — | — |
| 28a | — | 100 | 100 | 100 | 39 | 7 | 0 |
| 29 | — | — | — | — | — | — | — |
| 29a | — | 100 | 70 | 1 | 0 | 0 | — |
| 30 | — | — | — | — | — | — | — |
| 30a | — | 100 | 100 | 100 | 0 | 0 | — |
| 31 | 22 | — | 21 | — | 16 | — | 21 |
| 32 | — | — | — | — | — | — | — |
| 32a | — | 100 | 100 | 100 | 100 | 87 | — |
| 33 | — | — | — | — | — | — | — |
| 33a | 100 | — | 100 | — | 100 | — | 37 |
| 34 | — | — | — | — | — | — | — |
| 34a | 100 | — | 79 | — | 50 | — | 44 |
| 35 | — | — | — | — | — | — | — |
| 35a | not active at or below 8 lbs/A | | | | | | |
| 36 | — | — | — | — | — | — | — |
| 36a | 100 | — | 100 | — | 13 | — | 1 |
| 37 | — | — | — | — | — | — | — |
| 37a | — | — | — | 90 | 57 | — | — |
| 38 | — | — | — | — | — | — | — |
| 38a | — | — | — | 100 | 65 | 0 | 0 |
| 39 | — | — | — | — | — | — | — |
| 39a | 100 | — | 100 | — | 45 | — | 0 |
| 40 | — | — | — | — | — | — | — |
| 40a | 100 | — | 92 | — | 14 | — | 0 |
| 41 | not active at or below 8 lbs/A | | | | | | |

TABLE X-continued

Biological Data (Wheat Greenhouse Data)
% Male Sterility at Dosage (lbs./A)

| Example # | 8 | 4 | 2 | 1 | $\frac{1}{2}$ | $\frac{1}{4}$ | $\frac{1}{8}$ |
|---|---|---|---|---|---|---|---|
| 42 | — | — | — | — | — | — | — |
| 42a | 100 | — | 100 | — | 90 | — | 43 |
| 43 | — | — | — | — | — | — | — |
| 43a | 100 | — | 100 | — | 100 | — | 100 |
| 44 | — | — | — | — | — | — | — |
| 44a | 100 | — | 100 | — | 80 | — | 4 |
| 45 | — | — | — | — | — | — | — |
| 45a | 100 | — | 100 | — | 93 | — | 8 |
| 46 | — | — | — | — | — | — | — |
| 46a | 100 | — | 100 | — | 73 | — | 0 |
| 47 | — | — | — | — | — | — | — |
| 47a | 100 | — | 84 | — | 0 | — | 0 |
| 48 | 92 | — | 21 | — | 6 | — | 1 |
| 49 | 100 | — | 92 | — | 0 | — | 0 |
| 50 | — | 100 | 100 | 61 | 0 | — | — |
| 51 | 92 | — | 7 | — | 0 | — | 0 |
| 52 | 100 | — | 100 | — | 39 | — | 0 |
| 53 | 11.1 | — | 9.4 | — | 0 | — | 0 |
| 54 | No heads | — | 100 | — | 44.6 | — | 13.6 |
| 55 | 15.4 | — | 9.2 | — | 2.2 | — | 0 |
| 56 | 100 | — | 14 | — | 0 | — | 0 |
| 57 | 100 | — | 87.0 | — | 38.6 | — | 28.3 |
| 58 | 100 | — | 94.6 | — | 48.9 | — | 0 |
| 59 | 100 | — | 100 | — | 56.5 | — | 9.0 |
| 60 | 2.2 | — | 3.6 | — | 10.8 | — | 4.0 |
| 61 | 13.9 | — | 9.9 | — | 0 | — | 9.4 |
| 62 | 97.4 | — | 24.1 | — | 16.7 | — | 22.4 |
| 63 | 35.1 | — | 6.1 | — | 8.3 | — | 18.9 |
| 64 | 100 | — | 100 | — | 65.7 | — | 8.3 |
| 65 | — | — | 34.3 | — | 9.9 | — | 24.4 |
| 66 | 4.7 | — | 0 | — | 0 | — | 0 |
| 67 | 93.2 | — | 51.7 | — | 05.6 | — | 3.4 |
| 68 | 0 | — | 10.7 | — | 12.4 | — | 0 |
| 69 | 48.8 | — | 51.2 | — | 20.3 | — | 68 |
| 70 | 26.6 | — | 15.2 | — | 22.8 | — | 32.3 |
| 71 | 100 | — | 57.7 | — | 13.2 | — | 0 |
| 72 | 14.5 | — | 19.4 | — | 25 | — | 16 |
| 73 | 0 | — | 0 | — | 0 | — | 0 |
| 74 | 19.8 | — | 16.0 | — | 19.8 | — | 19 |
| | (32 lb/A-0% 8 lb/A-2.5% 2 lb/A-5.8%) | | | | | | |
| | (16 lb/A-6.2% 4 lb/A-0%) | | | | | | |
| 75 | 43.3 | — | 16.7 | — | 5.7 | — | 14.8 |
| 76 | 100 | — | 97.7 | — | 65.0 | — | 16.0 |
| 77 | — | — | — | — | — | — | — |
| 78 | 90.9 | — | 21.9 | — | 26.0 | — | 22.3 |
| 79 | 0 | — | 0 | — | 3 | — | 3 |
| 80 | — | — | — | — | — | — | — |
| 80a | 5 | — | 0 | — | 2 | — | 3 |
| 81 | — | — | — | — | — | — | — |
| 81a | — | 7 | 5 | 5 | 5 | 5 | 5 |
| 82 | 0 | — | 0 | — | 0 | — | — |
| 83 | — | — | — | — | — | — | — |
| 83a | 42 | — | 19 | — | 3 | — | 0 |
| 84 | — | — | — | — | — | — | — |
| 84a | 12 | — | — | — | — | — | — |
| 85 | — | — | — | — | — | — | — |
| 85a | 69 | — | 22 | — | 0 | — | 0 |
| 86 | — | — | — | — | — | — | — |
| 86a | 0 | — | 0 | — | 0 | — | 0 |
| 87 | 99 | — | 90 | — | 63 | — | 28 |
| 88 | — | — | — | — | — | — | — |
| 88a | 100 | — | 98 | — | 80 | — | 57 |
| 89 | — | — | — | — | — | — | — |
| 89a | 100 | — | 100 | — | 100 | — | 100 |
| 90 | — | — | — | — | — | — | — |
| 90a | 100 | — | 100 | — | 44 | — | 35 |
| 91 | — | — | — | — | — | — | — |
| 91a | 98 | — | 60 | — | 24 | — | 17 |
| 92 | — | — | — | — | — | — | — |
| 92a | 66 | — | 16 | — | 8 | — | 3 |
| 93 | — | — | — | — | — | — | — |
| 93a | — | — | 100 | — | 100 | — | 100 | 100 |
| 94 | — | — | — | — | — | — | — |
| 94a | 39 | — | 1 | — | 7 | — | 1 |
| 95 | 2 | — | 2 | — | 0 | — | 0 |
| 96 | — | — | — | — | — | — | — |
| 96a | 0 | — | 0 | 0 | 0 | — | 0 | — |
| 97 | — | — | — | — | — | — | — |
| 97a | 0 | — | 0 | — | 0 | — | 0 |
| 98 | 16 | — | 0 | — | 4 | — | 9 |
| 99 | 10 | — | — | — | — | — | — |
| 100 | — | — | — | — | — | — | — |
| 100a | — | 100 | 100 | 88 | 10 | — | — |
| 101 | — | — | — | — | — | — | — |
| 101a | 100 | — | 81 | — | 6 | — | 0 |
| 102a | 0 | 0 | 2 | — | — | — | — |
| 103 | 1 | — | 0 | — | 0 | — | 0 |
| 104 | — | — | — | — | — | — | — |
| 104a | — | 100 | 100 | 91 | 56 | 66 | — |
| 105 | — | — | — | — | — | — | — |
| 105a | — | 100 | 100 | 97 | 18 | 11 | — |
| 106 | — | — | — | — | — | — | — |
| 106a | 0 | — | 6 | — | 0 | — | 4 |
| 107 | — | — | — | — | — | — | — |
| 107a | 32 | — | 0 | — | 0 | — | 0 |
| 108 | — | — | — | — | — | — | — |
| 108a | — | — | 78 | — | 11 | — | 2 |
| 109 | — | — | — | — | — | — | — |
| 109a | — | — | 73 | — | 14.2 | — | 0 |

Table XI below depicts the male/female selectivity of several of the compounds of Group A, formula II, of the present invention. Application rates sufficient to effect high levels of male sterility maintain high levels of female fertility. Substantial loss of female fertility occurs only at overdose application rates

TABLE XI

Female Fertility, Culm Inhibition, Height Inhibition
(Wheat Greenhouse Data)

| Example # | Dosage (lbs/A) | % Sterility | % Culm Inhibition | % Spike Inhibition | % Female Fertility |
|---|---|---|---|---|---|
| 13a | 1 | 100 | 15 | 23 | — |
| | $\frac{1}{2}$ | 93 | 5 | 9 | 23 |
| | $\frac{1}{4}$ | 100 | 0 | 0 | 67 |
| | $\frac{1}{8}$ | 98 | 0 | 11 | 80 |
| | 1/16 | 10 | 0 | 0 | — |
| 16a | 1 | 100 | 50 | 28 | — |
| | $\frac{1}{2}$ | 100 | 40 | 14 | — |
| | $\frac{1}{4}$ | 100 | 20 | 14 | — |
| | $\frac{1}{8}$ | 100 | 25 | 9 | 70 |
| | 1/16 | 83 | 0 | 4 | — |
| 44a | 1 | 100 | 0 | 0 | 78 |
| | $\frac{1}{2}$ | 100 | 0 | 2 | 80 |
| | $\frac{1}{4}$ | 70 | 5 | 4 | — |
| | $\frac{1}{8}$ | 40 | 10 | 5 | — |

Other crops upon which compounds of the present invention have been shown to be effective are corn and barley.

The following procedures are used to evaluate the activity of the compounds of this invention for inducing male sterility in corn.

Four rows of inbred variety B-73 are interplanted with two rows of inbred variety Mo-17. Both lines are planted at a rate of 20,000 seeds/A. The chemicals of this invention are applied to variety B-73 several weeks later when the last leaf of the plant is just beginning to elongate and the tassel is approximately one inch long and not yet branched. All treatments are applied with a hand held pressurized sprayer equipped with a 3-nozzle boom containing D 3 disc/45 core Tee Jet cone spray tips. Each nozzle is directed at the row with one placed on either side and over the row. Triton[R] X-100 surfactant (a trademark of Rohm and Haas Company) at 0.03% is added as a surfactant. Dosage and carrier volume calculations are based on rows 36 inches wide.

Pollinating ability of treated plants is measured by crossing their pollen onto silks of untreated plants and recording the amount of see set.

Table XII below demonstrates the effect of compounds of Group A, formula II, of the present invention on the male sterility of field corn.

TABLE XII

| Example # | 8 | 4 | 2 | 1 | ½ | ¼ | ⅛ |
|---|---|---|---|---|---|---|---|
| 16a | — | 100 | 100 | 100 | 100 | 100 | — |

The compounds of Group A, formula II, of the present invention are also effective on barley.

Table XIV below demonstrates the male sterility obtained with one of the compounds of Group A, formula II, of the present invention on barley grain under greenhouse conditions. (Variety Park)

TABLE XIV

| Example # | ¼ | ⅛ | 1/16 | 1/32 |
|---|---|---|---|---|
| 16a | 100 | 96 | 95 | 88 |

Table XIV below sets forth field test data which demonstrate further the effect of several compounds of Group A, formula II, of the present invention on the male sterility of field corn (B-73).

TABLE XIV

% Male Sterility of Field Corn (Field Test Data)

| Example # | \% Male Sterility at Various Dosages (lbs/A) | | | | | | | |
|---|---|---|---|---|---|---|---|---|
| | 1/16 | ⅛ | ¼ | ½ | 1 | 2 | 4 | 8 |
| 43a | 100 | 100 | 100 | 100 | — | — | — | — |
| 16a | 13 | 67 | 99 | 100 | 100 | — | — | — |
| 16, K salt | 12 | 40 | 100 | 100 | 100 | — | — | — |
| 32a | 42 | 84 | 100 | 100 | — | — | — | — |
| 30a | — | 64 | 34 | 100 | 100 | — | — | — |
| 13a | — | 29 | 59 | 62 | 90 | 100 | 100 | — |
| 18a | — | — | 8 | 30 | 80 | 100 | 100 | — |
| 5a | — | — | 37 | 52 | 98 | 100 | 100 | — |
| 26a | — | — | 70 | 100 | 100 | 100 | 100 | — |
| 16 | Not active at 2 lb/A and below | | | | | | | |
| 4a | — | — | — | — | 12 | 67 | 88 | 100 |
| 14 | Not active at 8 lb/A and below | | | | | | | |

Table VIII below sets forth additional field test data which demonstrate further the effect of several compounds of the present invention on the male sterility and female sterility of field corn (B-73).

TABLE XV

% Male Sterility and % Female Fertility of Field Corn at Various Dosages (lbs/A) (Field Test Data)

| Example # | % Male Sterility | | | | | | % Fertility* | | | | | |
|---|---|---|---|---|---|---|---|---|---|---|---|---|
| | 1/16 | ⅛ | ¼ | ½ | 1 | 2 | 1/16 | ⅛ | ¼ | ½ | 1 | 2 |
| 16, K salt | 90 | 100 | 100 | 100 | 100 | 100 | G-E | G-E | G-E | G | P-F | P |
| 13, K salt | 27 | 58 | 62 | 88 | 86 | 100 | E | G-E | G-E | E | G | F-G |
| 43, K salt | 90 | 100 | 100 | 100 | 100 | — | G-E | G | F-G | G | G | — |
| 42, K salt | 16 | 46 | 72 | 100 | 100 | 100 | G-E | G | G | G | G | G |
| 32a | 82 | 100 | 100 | 100 | 100 | 100 | G-E | G | F | P | P | — |
| 30a | 52 | 65 | 65 | 59 | 47 | 34 | G-E | G | G-E | G | G-E | G |

*E = Excellent;
G = Good;
F = Fair;
P = Poor.

Table XVI below sets forth field test data which demonstrate the effect of several compounds of Group A, formula II, of the present invention on the male sterility and female sterility of sorghum (Inbred No. 6250).

TABLE XVI

% Male Sterility and % Female Fertility of Sorghum at Various Dosages (lbs/A) (Field Test Data)

| Example # | % Sterility | | | | % Fertility* | | | |
|---|---|---|---|---|---|---|---|---|
| | ⅛ | ¼ | ½ | 1 | ⅛ | ¼ | ½ | 1 |
| 16, K salt | 97 | 99 | 100 | 100 | E | E | E | F |
| 43, K salt | 100 | 100 | 100 | 100 | P | P | P | P |
| 42, K salt | 83 | 98 | 100 | 100 | E | E | E | G |

*E = Excellent; G = Good; F = Fair; P = Poor.

Table XVII below sets forth additional field test data which demonstrate the effective of several compounds of Group A, formula II, of the present invention on male sterility and female fertility of sorghum (Inbred No. 7078).

TABLE XVII

% Male Sterility and % Female Fertility on Sorghum at Various Dosages (lbs/A) (Field Test Data)

| Example # | % Male Sterility | | | | % Female Fertility* | | | |
|---|---|---|---|---|---|---|---|---|
| | ⅛ | ¼ | ½ | 1 | ⅛ | ¼ | ½ | 1 |
| 16, K salt | 35 | 73 | 95 | 100 | E | E | G | F |
| 43, K salt | 100 | 100 | 100 | 100 | E | F | P | P |
| 42, K salt | 9 | 34 | 91 | 100 | E | E | E | F |

*E = Excellent; G = Good; F = Fair; P = Poor.

Table XVII below sets forth field test data which demonstrate the effect of several compounds of Group A, formula II, of the present invention on male sterility and female fertility of barley (Variety Henry).

TABLE XVIII

% Male Sterility and % Female Fertility of Barley at Various Dosages (lbs/A) (Field Test Data)

| Example # | % Sterility | | | | % Fertility | | | |
|---|---|---|---|---|---|---|---|---|
| | ⅛ | ¼ | ½ | 1 | ⅛ | ¼ | ½ | 1 |
| 16, K salt | 32 | 56 | 92 | 99 | 93 | 96 | 75 | 56 |
| 13, K salt | 2 | 4 | 4 | 8 | 95 | 100 | 100 | 96 |
| 43, K salt | 4 | 22 | 48 | 77 | 99 | 97 | 94 | 76 |
| 42, K salt | 3 | 4 | 4 | 43 | 96 | 100 | 100 | 81 |

Table XIX illustrates the activity of a representative compound according to this invention in corn.

TABLE XIX
Sterilant Activity in Corn

| Compound | Dosage Rate | % Sterility | Height Inhibition |
|---|---|---|---|
| (Example 50) | 12 | 100 | 18 |
| | 8 | 97 | 11 |
| | 4 | 17 | 0 |
| | 2 | 1 | 0 |
| | 1 | 0 | 0 |

Table XX below sets forth field test data which illustrates the activity of representative compounds of Group C, formula XXXI, of the present invention on male sterility of barley.

TABLE XX

| Example | 8 | 4 | 2 | 1 | ½ | ¼ |
|---|---|---|---|---|---|---|
| 88a | — | 100 | 100 | 100 | 58 | — |
| 89a | — | — | 100 | 100 | 100 | 100 |

Table XXI below sets forth field test data which illustrates the activity of a representative compound of Group C, formula XXXI, of the present invention on male sterility of corn.

TABLE XXI

| Example | 12 | 4 |
|---|---|---|
| 88a | 100 | 100 |

Table XXII below sets forth field test data which illustrates the culm inhibition activity of several representative compounds of Group C, formula XXXI, of the present invention on barley.

TABLE XXII
CULM INHIBITION (BARLEY) % INHIBITION AT RATE, LB/A

| Example | 8 | 4 | 2 | 1 | ½ | ¼ |
|---|---|---|---|---|---|---|
| 88a | — | 70 | 70 | 60 | 40 | — |
| 89a | — | — | 50 | 50 | 50 | 50 |

Table XXIII below presents field test data which illustrates the height inhibition activity of a representative compound of Group C, formula XXXI, of the present invention on corn.

TABLE XVII
HEIGHT INHIBITION, % INHIBITION AT RATE, LB/A

| Example | 12 | 4 |
|---|---|---|
| 88a | 57 | 43 |

Table XXIV below sets forth field test data which illustrates the effect of several representative compounds of Group D, formula XXXII, of the present invention as male sterility of corn.

TABLE XXIV
CORN, % MALE STERILITY AT RATE, LB/A

| Example | 4 | 2 | 1 | ½ | ¼ | ⅛ |
|---|---|---|---|---|---|---|
| 100a | — | 100 | 80 | 62 | 85 | — |
| 101a | 100 | 96 | 96 | 74 | 6 | — |
| 105a | — | — | 100 | 100 | 28 | 25 |

Table XXV below sets forth field test data which illustrates the effect of a representative compound of Group D, formula XXXII, of the present invention on male sterility of barley

TABLE XXV

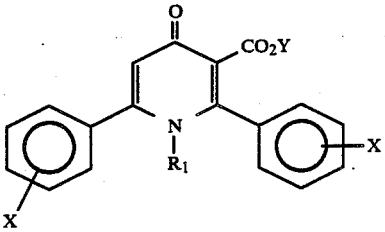

BARLEY, % MALE STERILITY AT RATE, LB/A

| Example | 8 | 4 | 2 | 1 | ½ | ¼ | ⅛ |
|---|---|---|---|---|---|---|---|
| 105a | — | — | 100 | 100 | 100 | 100 | — |

Table XXVI below sets forth field test data which demonstrates the culm inhibition activity of several representative compounds of Group C, formula XXXI, of the present invention on wheat.

TABLE XXVI
CULM INHIBITION (WHEAT), % INHIBITION AT RATE, LB/A

| Example | 8 | 4 | 2 | 1 | ½ | ¼ | ⅛ | 1/16 | 1/32 | 1/64 |
|---|---|---|---|---|---|---|---|---|---|---|
| 89a | — | — | — | — | — | — | 35 | 35 | 35 | 35 |
| 90a | 80 | — | 60 | — | 40 | — | 35 | — | — | — |
| 91a | 50 | — | 45 | — | 30 | — | 10 | — | — | — |
| 92a | 40 | — | 30 | — | 10 | — | 15 | — | — | — |
| 93a | — | — | 80 | — | 75 | — | 75 | — | — | 50 |

What is claimed is:

1. A method for inducing male sterility in a cereal grain plant which comprises treating the plant prior to meiosis with an amount effective to produce male sterility in the plant of a compound according to the formula:

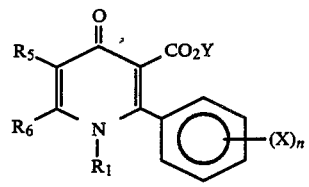

wherein
$R_1$ is $(C_1$–$C_6)$ alkyl group or a $(C_2$–$C_6)$ alkenyl group unsubstituted or optionally substituted with a member selected from a hydroxy group, a carboxy group, a phenyl group or a phenyl group substituted with up to two substituents selected from halogen, methyl, ethyl, methoxy, ethoxy, trifluoromethyl, nitro and cyano;
$R_5$ is a hydrogen atom, $(C_1$–$C_6)$ alkyl group or a halogen atom;
$R_6$ is a hydrogen atom or a $(C_1$–$C_6)$ alkyl group;
Y is a hydrogen atom or a $(C_1$–$C_6)$ alkyl group;
X is a hydrogen or halogen atom, a trihalomethyl, a $(C_1$–$C_6)$ alkyl, a nitro, a cyano, or a $(C_1$–$C_4)$ alkoxy group and
n is the integer 1, 2 and 3;
or an agronomically acceptable salt thereof.

2. A method for inducing male sterility in a cereal grain plant which comprises treating the plant prior to meiosis with an amount effective to produce male sterility in the plant of a compound according to the formula:

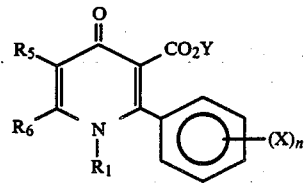

wherein
$R_1$ is a $(C_1-C_6)$ alkyl or allyl group;
$R_5$ is a hydrogen atom, $(C_1-C_6)$ alkyl group or a halogen atom;
$R_6$ is a $(C_1-C_6)$ alkyl group;
Y is a hydrogen atom or a $(C_1-C_6)$ alkyl group;
X is a hydrogen or a halogen atom, a trihalomethyl, a $(C_1-C_6)$ alkyl, a nitro, a cyano, or a $(C_1-C_4)$ alkoxy group; and
n is the integer 1, 2 or 3;
or an agronomically acceptable salt thereof.

* * * * *